(12) United States Patent
Kuyler et al.

(10) Patent No.: US 11,612,497 B2
(45) Date of Patent: Mar. 28, 2023

(54) SPINAL IMPLANT SYSTEM AND METHOD

(71) Applicant: WARSAW ORTHOPEDIC INC., Warsaw, IN (US)

(72) Inventors: Adriaan J. Kuyler, St. Augustine, FL (US); Anthony J. Melkent, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 212 days.

(21) Appl. No.: 16/984,417

(22) Filed: Aug. 4, 2020

(65) Prior Publication Data

US 2020/0360151 A1    Nov. 19, 2020

Related U.S. Application Data

(62) Division of application No. 14/923,152, filed on Oct. 26, 2015, now Pat. No. 10,779,955.

(51) Int. Cl.
*A61F 2/44* (2006.01)
*A61F 2/30* (2006.01)

(52) U.S. Cl.
CPC ............ *A61F 2/447* (2013.01); *A61F 2/4455* (2013.01); *A61F 2002/3008* (2013.01); *A61F 2002/30062* (2013.01); *A61F 2002/30065* (2013.01); *A61F 2002/30092* (2013.01); *A61F 2002/3093* (2013.01); *A61F 2002/30383* (2013.01); *A61F 2002/30405* (2013.01); *A61F 2002/30471* (2013.01); *A61F 2002/30507* (2013.01); *A61F 2002/30538* (2013.01); *A61F 2002/30556* (2013.01); *A61F 2002/30579* (2013.01); *A61F 2002/30841* (2013.01); *A61F 2002/30904* (2013.01); *A61F 2310/00017* (2013.01); *A61F 2310/00023* (2013.01); *A61F 2310/00029* (2013.01); *A61F 2310/00071* (2013.01); *A61F 2310/00077* (2013.01); *A61F 2310/00179* (2013.01); *A61F 2310/00293* (2013.01); *A61F 2310/00359* (2013.01)

(58) Field of Classification Search
CPC ............ A61F 2/447; A61F 2/4455; A61F 2002/30405; A61F 2002/30471; A61F 2002/30538; A61F 2002/30904; A61F 2002/30937; A61F 2002/30556; A61F 2002/30579; A61F 2002/30383
USPC .......................................... 623/17.11–17.16
See application file for complete search history.

(56) References Cited

U.S. PATENT DOCUMENTS 7,850,733 B2    12/2010    Baynham et al.
7,875,078 B2    1/2011    Wysocki et al.
7,909,869 B2    3/2011    Gordon et al.
(Continued)

*Primary Examiner* — Marcela I. Shirsat
(74) *Attorney, Agent, or Firm* — Sorell, Lenna & Schmidt, LLP

(57) ABSTRACT

A spinal implant comprises a first member, a second member and an actuator defining a transverse pivot axis, A first link is connected to the first member and the actuator adjacent the pivot axis. The first link includes an inner surface defining a cavity. A second link is connected to the second member and the actuator adjacent the pivot axis. The actuator is rotatable for translating the pivot axis such that the second link is movable within the cavity to move the members between a contracted configuration and an expanded configuration. Systems and methods of use are disclosed.

20 Claims, 21 Drawing Sheets

(56) References Cited

U.S. PATENT DOCUMENTS

| | | |
|---|---|---|
| 8,062,375 B2 * | 11/2011 | Glerum ............... A61F 2/447 606/279 |
| 8,105,358 B2 | 1/2012 | Phan |
| 8,105,382 B2 | 1/2012 | Olmos et al. |
| 8,123,810 B2 | 2/2012 | Gordon et al. |
| 8,133,232 B2 | 3/2012 | Levy et al. |
| 8,187,332 B2 | 5/2012 | Mcluen |
| 8,382,842 B2 | 2/2013 | Greenhalgh et al. |
| 8,394,145 B2 | 3/2013 | Weiman |
| 8,398,713 B2 | 3/2013 | Weiman |
| 8,403,990 B2 | 3/2013 | Dryer et al. |
| 8,435,298 B2 | 5/2013 | Weiman |
| 8,491,659 B2 | 7/2013 | Weiman |
| 8,518,120 B2 | 8/2013 | Glerum et al. |
| 8,523,944 B2 | 9/2013 | Jimenez et al. |
| 8,556,979 B2 | 10/2013 | Glerum et al. |
| 8,568,481 B2 | 10/2013 | Olmos |
| 8,628,577 B1 | 1/2014 | Jimenez |
| 8,628,578 B2 | 1/2014 | Miller et al. |
| 8,632,595 B2 | 1/2014 | Weiman |
| 8,663,329 B2 | 3/2014 | Ernst |
| 8,679,183 B2 | 3/2014 | Glerum et al. |
| 8,685,098 B2 | 4/2014 | Glerum et al. |
| 8,709,086 B2 | 4/2014 | Glerum et al. |
| 8,778,025 B2 | 7/2014 | Ragab et al. |
| 8,795,366 B2 | 8/2014 | Varela |
| 8,888,853 B2 | 11/2014 | Glerum et al. |
| 8,888,854 B2 | 11/2014 | Glerum et al. |
| 8,894,711 B2 | 11/2014 | Varela |
| 8,894,712 B2 | 11/2014 | Varela |
| 8,926,704 B2 | 1/2015 | Glerum |
| 8,940,049 B1 | 1/2015 | Jimenez |
| 9,039,771 B2 | 5/2015 | Glerum et al. |
| 9,119,730 B2 | 9/2015 | Glerum et al. |
| 2011/0054621 A1 | 3/2011 | Lim |
| 2011/0172721 A1 | 7/2011 | Varela |
| 2011/0172774 A1 | 7/2011 | Varela |
| 2012/0035729 A1 | 2/2012 | Glerum et al. |
| 2012/0109319 A1 | 5/2012 | Perisic |
| 2012/0150304 A1 | 6/2012 | Glerum et al. |
| 2012/0150305 A1 | 6/2012 | Glerum et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2013/0144388 A1 | 6/2013 | Emery et al. |
| 2013/0158664 A1 * | 6/2013 | Palmatier ............... A61F 2/4425 623/17.16 |
| 2014/0121774 A1 | 5/2014 | Glerum et al. |
| 2014/0324171 A1 | 10/2014 | Glerum et al. |
| 2015/0272743 A1 * | 10/2015 | Jimenez ............... A61F 2/447 623/17.16 |
| 2016/0120660 A1 * | 5/2016 | Melkent ............... A61F 2/447 623/17.16 |
| 2017/0156885 A1 * | 6/2017 | Zur ............... A61F 2/4611 |

* cited by examiner

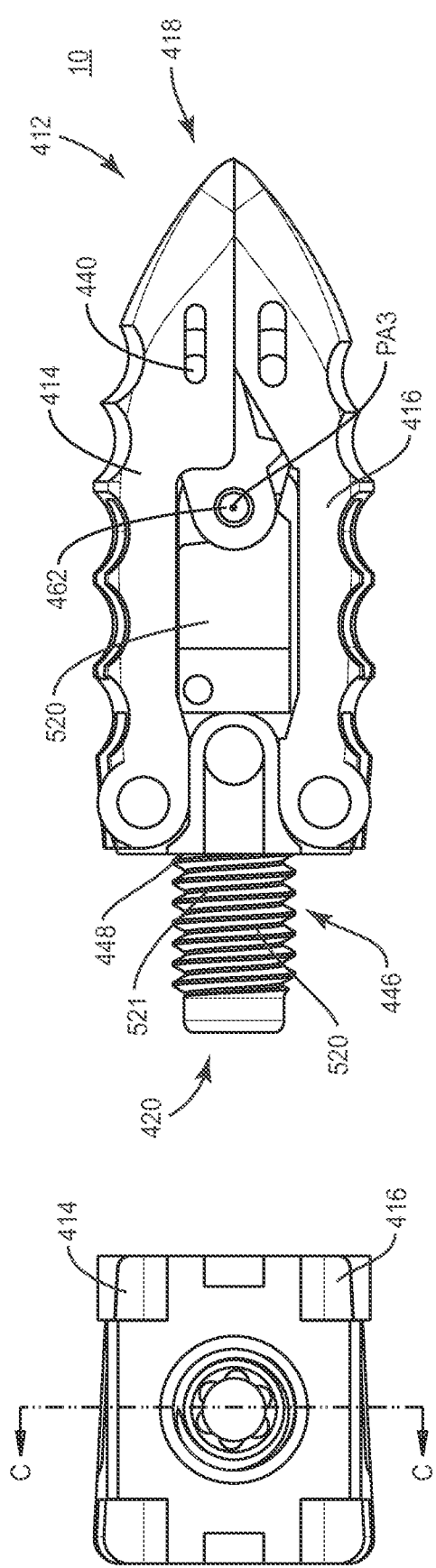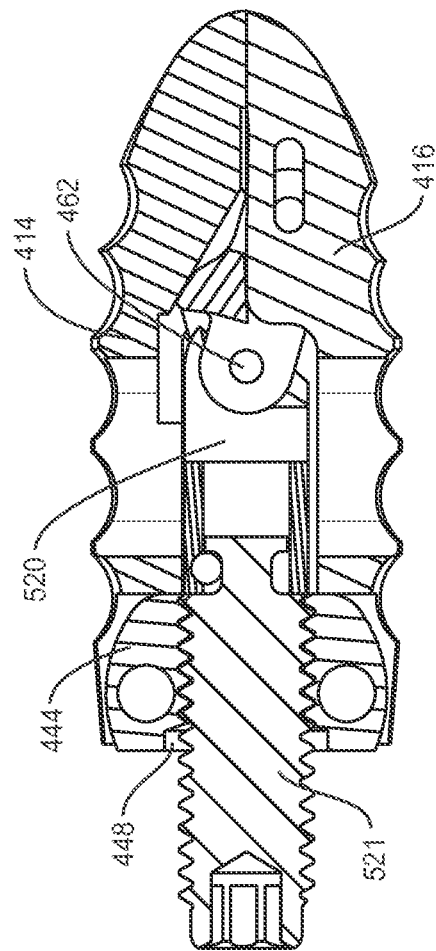
FIG. 19
FIG. 20
FIG. 21

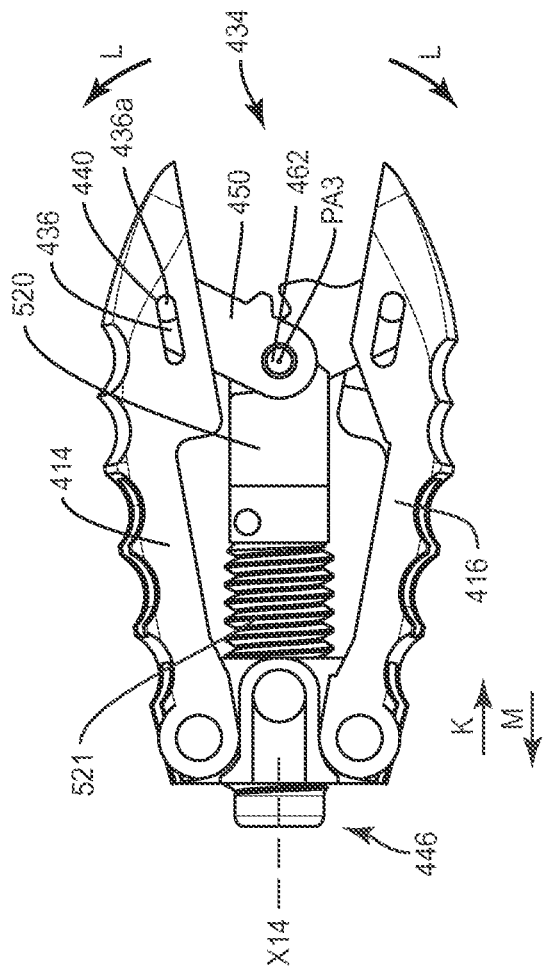
FIG. 24
FIG. 25
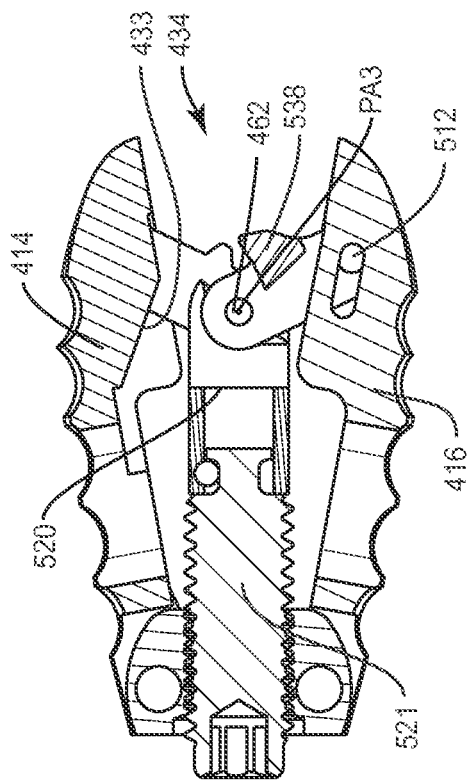
FIG. 26
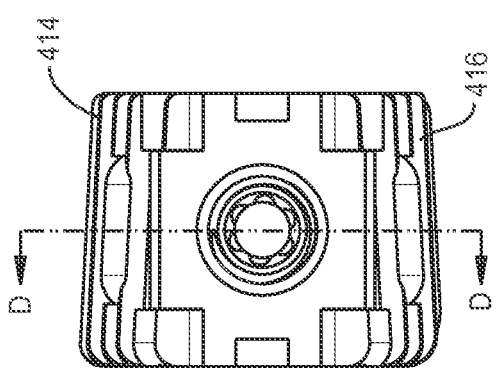

SPINAL IMPLANT SYSTEM AND METHOD

CROSS-REFERENCE TO RELATED APPLICATION

This application is a divisional of U.S. patent application Ser. No. 14/923,152, filed Oct. 26, 2015, which is expressly incorporated herein by reference, in its entirety.

TECHNICAL FIELD

The present disclosure generally relates to medical devices for the treatment of musculoskeletal disorders, and more particularly to a surgical system that includes a spinal implant and a method for treating a spine.

BACKGROUND

Spinal disorders such as degenerative disc disease, disc herniation, osteoporosis, spondylolisthesis, stenosis, scoliosis and other curvature abnormalities, kyphosis, rumor, and fracture may result from factors including trauma, disease and degenerative conditions caused by injury and aging, Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, partial or complete discectomy, corpectomy and laminectomy, and implantable prosthetics. As part of these surgical treatments, spinal constructs, such as, for example, bone fasteners, spinal rods and interbody devices can be used to provide stability to a treated region. For example, during surgical treatment, interbody implants can be delivered to a surgical site for fixation with bone to immobilize a joint. Such interbody implants can include bone growth promoting material to enhance fixation of the interbody implants with the bone. This disclosure describes an improvement over these technologies.

SUMMARY

In one embodiment, a spinal implant is provided. The spinal implant comprises a first member, a second member and an actuator defining a transverse pivot axis. A first link is connected to the first member and the actuator adjacent the pivot axis. The first link includes an inner surface defining a cavity. A second link is connected to the second member and the actuator adjacent the pivot axis. The actuator is rotatable for translating the pivot axis such that the second link is movable within the cavity to move the members between a contracted configuration and an expanded configuration. In some embodiments, systems and methods are disclosed.

BRIEF DESCRIPTION OF THE DRAWINGS

The present disclosure will become more readily apparent from the specific description accompanied by the following drawings, in which:

FIG. 19 is a side view of components of one embodiment of a spinal implant system in accordance with the principles of the present disclosure;

FIG. 20 is an end view of the components shown in FIG. 19;

FIG. 21 is a cross section view of the components shown in FIG. 20 taken along lines C-C;

FIG. 24 is a side view of the components shown in FIG. 19;

FIG. 25 is an end view of the components shown in FIG. 19;

FIG. 26 is a cross section view of the components shown in FIG. 25 taken along lines D-D;

DETAILED DESCRIPTION

Figure 1:
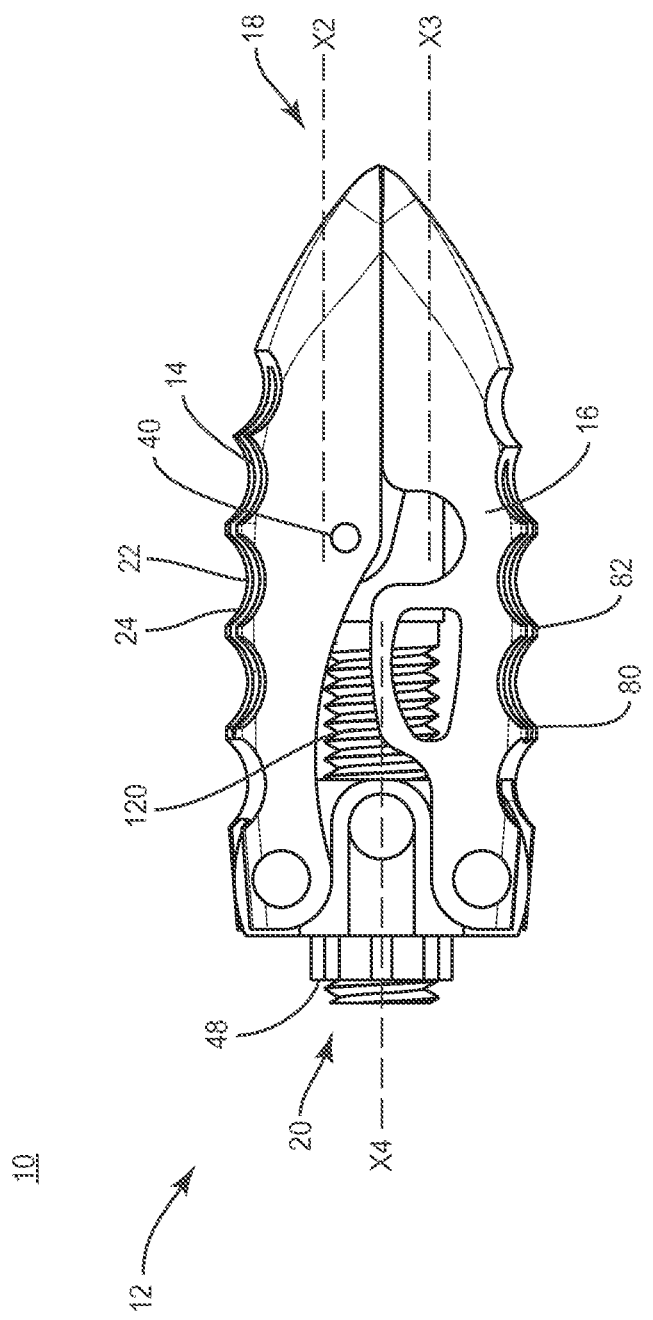
FIG. 1 is a side view of components of one embodiment of a spinal implant system in accordance with the principles of the present disclosure.
Figure 2:
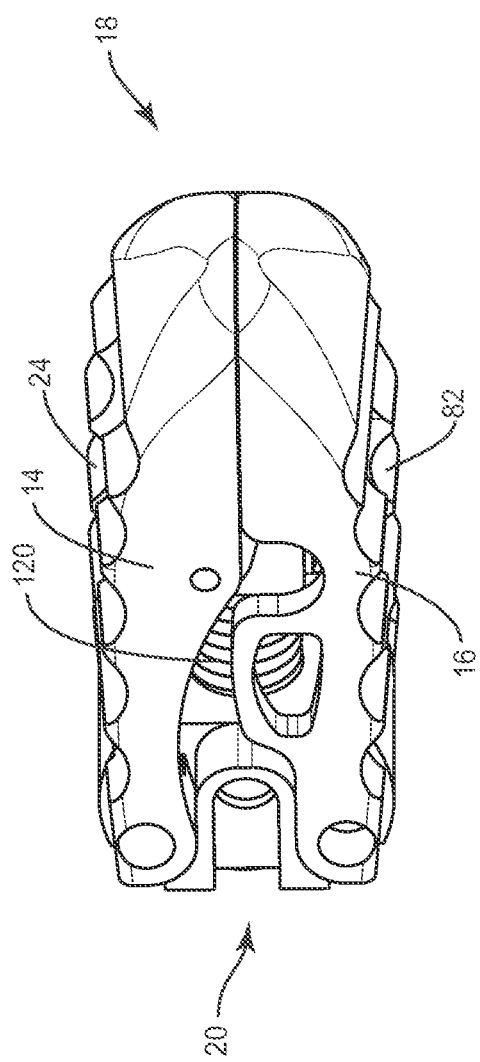
FIG. 2 is a perspective view of the components shown in FIG. 1.
Figure 3:
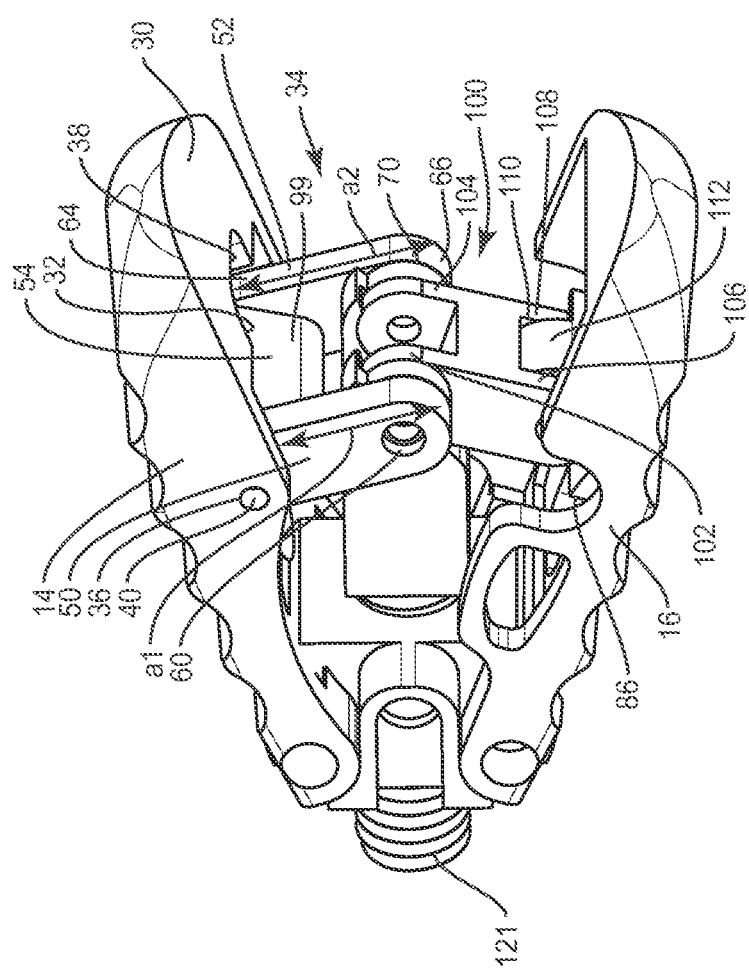
FIG. 3 is a perspective view of the components shown in FIG. 1.

The exemplary embodiments of the surgical system and related methods of use disclosed are discussed in terms of medical devices for the treatment of musculoskeletal disorders and more particularly, in terms of a surgical system that includes a spinal implant and a method for treating a spine.

In some embodiments, the surgical system includes a spinal implant, such as, for example, an interbody implant. In some embodiments, the surgical system includes a spinal implant, such as, for example, an expanding linkage interbody device. In some embodiments, the surgical system comprises a spinal implant including an interbody implant having a linkage expansion mechanism. In some embodiments, the linkage is actuated by an actuator, such as, for example, a screw. In some embodiments, the interbody implant includes a linkage expansion mechanism and members, as described herein, that are unilaterally expandable, for example, a first member can be fixed in parallel with an actuator axis.

In some embodiments, the surgical system includes an interbody implant having one or a plurality of expansion zones. In some embodiments, the surgical system includes an interbody implant having a first expansion zone and a second expansion zone. In some embodiments, the interbody implant includes a first mechanism for expansion of the interbody implant in the first expansion zone and a second mechanism for expansion of the interbody implant in the second expansion zone. In some embodiments, the mechanisms of expansion are different. In some embodiments, the mechanisms of expansion are the same.

In some embodiments, the interbody implant includes one or more pins and angled slots for expansion of the interbody implant in the first expansion zone. In some embodiments, the pin can comprise a single component and/or a monolithic configuration, or include a plurality of components. In some embodiments, the interbody implant includes one or more protrusions and ramps for expansion of the interbody implant in the first expansion zone. In some embodiments, the interbody implant includes pivoting links for expansion of the interbody implant in the second expansion zone. In some embodiments, this configuration of the interbody implant allows for increased expansion height of the interbody implant and/or allows for disposal of the links at a minimum initial angle. In some embodiments, the minimum angle provides a reduction of stresses in one or more components of the interbody implant. In some embodiments, the links of the interbody implant, as described herein, are relatively disposed at a minimum angle and/or no less than an angle of 20 degrees. In some embodiments, the links of the interbody implant, as described herein, are relatively disposed at a minimum angle and/or no less than an angle of 20 degrees when the interbody implant is bearing load. In some embodiments, the links of the interbody implant, as described herein, are relatively disposed at an angle in a range of greater than 20 angular degrees. In some embodiments, the links of the interbody implant, as described herein, are relatively disposed at an angle that remains constant in the first expansion zone. In some embodiments, the links of the interbody implant, as described herein, are relatively disposed at an angle that increases in the first expansion zone.

In some embodiments, the interbody implant has one or a plurality of expansion rates for the first expansion zone and one or a plurality of expansion rates for the second expansion zone. In some embodiments, the expansion rates for the zones are different. In some embodiments, the expansion rates for the zones are the same. In some embodiments, the interbody implant has a uniform or linear expansion rate for the first expansion zone. In some embodiments, the interbody implant has a variable or graphically curved expansion rate for the first expansion zone. In some embodiments, the interbody implant has a uniform or linear expansion rate for the second expansion zone. In some embodiments, the interbody implant has a variable or graphically curved expansion rate for the second expansion zone. In some embodiments, the interbody implant includes curved surfaces for the ramps in the first expansion zone to reduce linearity of one or more of the expansion rates. In some embodiments, the interbody implant includes a decreased angle between links to increase linearity of one or more of the expansion rates in the second expansion zone. In some embodiments, the interbody implant includes an increased length of links to increase linearity of one or more of the expansion rates in the second expansion zone.

In some embodiments, the interbody implant has a linkage including two links. In some embodiments, the interbody implant has a linkage including one or a plurality of multiple link arrangements. In some embodiments, the linkage includes a pair of two link arrangements. In some embodiments, the linkage is drawn and/or pulled by an actuator to expand and/or contract the interbody implant. In some embodiments, the linkage is translated forward by an actuator to expand and/or contract or collapse the interbody implant. In some embodiments, the linkage is translated forward to expand and contract or collapse the interbody implant. In some embodiments, the linkage is engaged with the interbody implant by pins. In some embodiments, the pins are engaged with slots disposed with the interbody implant to facilitate expansion and/or contraction or collapse.

In some embodiments, the interbody implant has a linkage that is stationary during a portion of expansion and then the linkage is actuated to expand. In some embodiments, the actuator includes an engagement portion, such as, for example, a torx connection configured to facilitate expansion and contraction.

In some embodiments, the interbody implant includes a dynamic slot configured for engagement and guidance of the linkage. In some embodiments, the linkage translates within the slot to drive the interbody implant between expansion and/or contraction. In some embodiments, the slot is disposed at an angle to drive the interbody implant between an expanded and/or contracted configuration. In some embodiments, the linkage translates along the angled slot.

In some embodiments, the interbody implant includes a quad link arrangement configured to control angular orientation of surfaces of the interbody implant to facilitate lordosis. In some embodiments, the linkage includes arms. In some embodiments, the arms include equal dimensions. In some embodiments, the arms are configured with different dimensions. In some embodiments, the varied dimension arms are configured to form an undulating interbody implant surface.

In some embodiments, the surgical system may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system may be employed with other osteal and bone related applications, including those associated with diagnostics and therapeutics. In some embodiments, the present system may be alternatively employed in a surgical treatment with a patient in a prone or supine position, and/or employ various surgical approaches to the spine, including anterior, posterior, posterior mid-line, direct lateral, postero-lateral, and/or antero lateral approaches, and in other body regions. The present disclosure may also be alternatively employed with procedures for treating the lumbar, cervical, thoracic, sacral and pelvic regions of a spinal column. The present system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro-discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

The following discussion includes a description of a surgical system including one or more spinal implants, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1-4, there are illustrated components of a surgical system, such as, for example, a spinal implant system 10 including a spinal implant, such as, for example, an interbody implant 12.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a minimally invasive procedure, including percutaneous techniques, mini-open and open surgical techniques to deliver and introduce one or more spinal implants, such as, for example, interbody implant 12, at a surgical site within a body of a patient, for example, a section of a spine. In some embodiments, spinal implant system 10 may be employed with surgical procedures, as described herein, and/or, for example, surgical procedures including corpectomy, discectomy, fusion and/or fixation treatments that employ spinal implants to restore the mechanical support function of vertebrae.

Interbody implant 12 includes a member 14 and a member 16. Interbody implant 12 extends between an end 18 and an end 20. Member 14 defines a longitudinal axis X2. Member 14 includes a surface 22 that defines a vertebral engaging surface 24. In some embodiments, the cross-sectional geometry of member 14 may have various configurations, such as, for example, round, oval, oblong, triangular, polygonal having planar or arcuate side portions, irregular, uniform, non-uniform, consistent, variable, horseshoe shape, U-shape or kidney bean shape. In some embodiments, surface 24 may be smooth, even, rough, textured, porous, semi-porous, dimpled and/or polished. In some embodiments, surface 24 may include tissue penetrating members, such as, for example, a plurality of teeth. In some embodiments, the teeth may have various configurations, for example, round, oval, rectangular, polygonal, irregular, tapered, offset, staggered, uniform and non-uniform.

Member 14 and member 16 are connected by a linkage 34, as described herein. Member 14 includes a surface 30 that defines a cavity 32 configured for disposal of a portion of linkage 34, as described herein. Surface 30 defines openings 36, 38 configured for disposal of a connecting element, such, as for example, a pin 40, as described herein. Member 14 is configured for relative rotation about pin 40 upon actuation of linkage 34, as described herein.

Surface 30 defines a cavity 42. Cavity 42 is in communication with a cavity 94 of member 16. Cavities 42, 94 are configured for disposal of a body, such as, for example, a housing 44, as described herein. Housing 44 is configured to connect member 14 with member 16. Housing 44 and cavities 42, 94 are configured for moveable disposal of an actuator, which includes a nut 46, as described herein, Housing 44 and cavities 42, 94 are configured for movable disposal of nut 46, as described herein. An opening 48 is disposed at end 20 and is in communication with cavities 42, 94. Opening 48 is configured for disposal of a portion of nut 46, as described herein.

Linkage 34 includes one or a plurality of links. Linkage 34 has a link 99, which includes an arm 50 and an arm 52. Arm 52 is spaced apart in relation to arm 50 to define a cavity 54. Arm 50 includes a length a1. Cavity 54 is configured for disposal of a complimentary link 100. Link 100 is movable between arms 50, 52. Arm 50 extends between an end 56 and an end 58. End 56 includes an opening (not shown) configured for engagement with pin 40. End 58 includes an opening 60 configured for engagement with a pin 62, as described herein. Pin 62 connects linkage 34 with nut 46 at a pivot axis PA. Pivot axis PA is disposed transverse to an axis of nut 46, as described herein. Pin 62 is connected with nut 46 to actuate rotation of members 14, 16, as described herein. In some embodiments, pin 62 includes a single component and/or a monolithic configuration. In some embodiments, pin 62 includes a plurality, of components.

Arm 52 extends between an end 64 and an end 66. End 64 includes an opening (not shown) configured for engagement with pin 40. End 66 includes an opening 70 configured for engagement with pin 62, as described herein. Arm 52 includes a length a2. In some embodiments, length a1 is equal to length a2. In some embodiments, length a1 is longer than length a2. In some embodiments, length a1 is shorter than length a2, In some embodiments, a non-equal length a1 and length a2 configuration facilitates adjustable spacing of vertebrae by interbody implant 12 to provide a variable lordotic implant. Each arm 50, 52 may have a variety of shapes and configurations. Arms 50, 52 are configured for connection with member 14 via pin 40 such that actuation of linkage 34 is configured to relatively rotate members 14, 16.

Member 16 defines a longitudinal axis X3. Member 16 includes a surface 80 that defines a vertebral engaging surface 82. In some embodiments, the cross-sectional geometry of member 16 may have various configurations, such as, for example, round, oval, oblong, triangular, polygonal having planar or arcuate side portions, irregular, uniform, non-uniform, consistent, variable, horseshoe shape, U-shape or kidney bean shape. In some embodiments, surface 82 may be smooth, even, rough, textured, porous, semi-porous, dimpled and/or polished. In some embodiments, surface 82 may include tissue penetrating members, such as, for example, a plurality of teeth. In some embodiments, the teeth may have various configurations, for example, round, oval, rectangular, polygonal, irregular, tapered, offset, staggered, uniform and non-uniform.

Member 16 includes a surface 84 that defines a cavity 86 configured for disposal of a portion of linkage 34, such as, for example, link 100. Link 100 includes a substantially H-shape and includes an arm 102, an arm 104, an arm 106 and an arm 108. Arm 102 is spaced apart in relation to arm 104. In some embodiments, arms 102, 104 define a cavity configured for moveable disposal of link 99. Arm 102 includes an opening (not shown) configured for disposal of pin 62. Arm 104 includes an opening (not shown) configured for disposal of pin 62, Link 100 is configured to pivot relative to link 34 about pin 62 to expand and contract or collapse interbody implant 12.

Arm 106 is spaced apart in relation to arm 108. Arms 106, 108 define a cavity 110 configured for disposal of a housing 112 and a pin 112p. Pin 112p is configured to facilitate rotation of link 100 relative to member 16 about pin 112p. Each arm 102, 104, 106, 108 may have a variety of shapes and configurations.

Surface 84 defines cavity 94. Cavity 94 is configured for disposal of housing 44 and nut 46, as described herein. The actuator includes a screw housing 120 and a screw 121 connected therewith. Screw 121 is threaded with, and rotates relative to and within screw housing 120. Screw housing 120 and screw 121 define an axis X4. Axis X4 extends parallel to axes X2, X3 when interbody implant 12 is in a contracted or collapsed configuration. Screw housing 120 is connected with pin 62 at pivot axis PA. Pivot axis PA is disposed transverse to axis X4.

Nut 46 is engageable with a surgical instrument, such as, for example, a driver (not shown). Screw 121 is threaded with nut 46 and within housing 44 for axial translation relative to nut 46 and housing 44. As the driver engages and rotates nut 46, nut 46 remains axially fixed adjacent end 20. Screw 121 translates relative to housing 44 such that screw 121/screw housing 120 translate and/or drive pin 62 and pivot axis PA axially relative to members 14, 16. Axial translation of pivot axis PA relatively rotates links 99, 100 to facilitate expansion and contraction of members 14, 16 about pivot axis PA.

Figure 4:
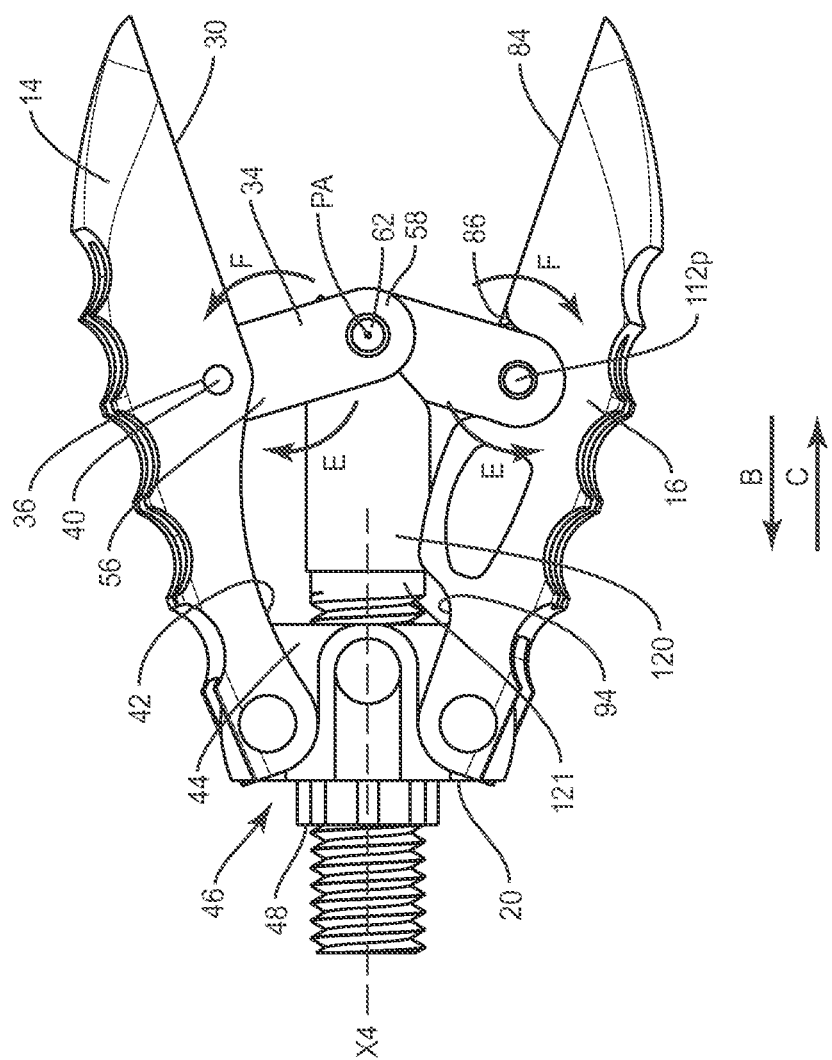
FIG. 4 is a side view of the components shown in FIG. 1.

In some embodiments, to expand interbody implant 12, nut 46 is rotated in a clockwise direction and screw 121 translates in an axial direction, such as, for example, a direction shown by arrow B in FIG. 4, relative to housing 44 via the threaded engagement within nut 46. Translation of screw 121 translates screw housing 120 and pivot axis PA, in a direction shown by arrow B, to draw linkage 34 in the axial direction to relatively rotate links 99, 100 about pivot axis PA, as shown by arrows E in FIG. 4. As links 99, 100 pivot about pivot axis PA, link 99 pivots about pin 40 and link 100 pivots about pin 62, causing members 14, 16 to expand.

In some embodiments, to contract or collapse interbody implant 12, nut 46 is rotated in a counter-clockwise direction and screw 121 translates in an axial direction, such as, for example, a direction shown by arrow C in FIG. 4, relative to housing 44 via the threaded engagement within nut 46. Translation of screw 121 translates screw housing 120 and pivot axis PA, in the direction shown by arrow C, to draw linkage 34 in the axial direction to relatively rotate links 99, 100 about pivot axis PA, as shown by arrows F in FIG. 4. As links 99, 100 pivot about pivot axis PA, link 99 pivots about pin 40 and link 100 pivots about pin 62, causing members 14, 16 to contract or collapse.

Figure 5:
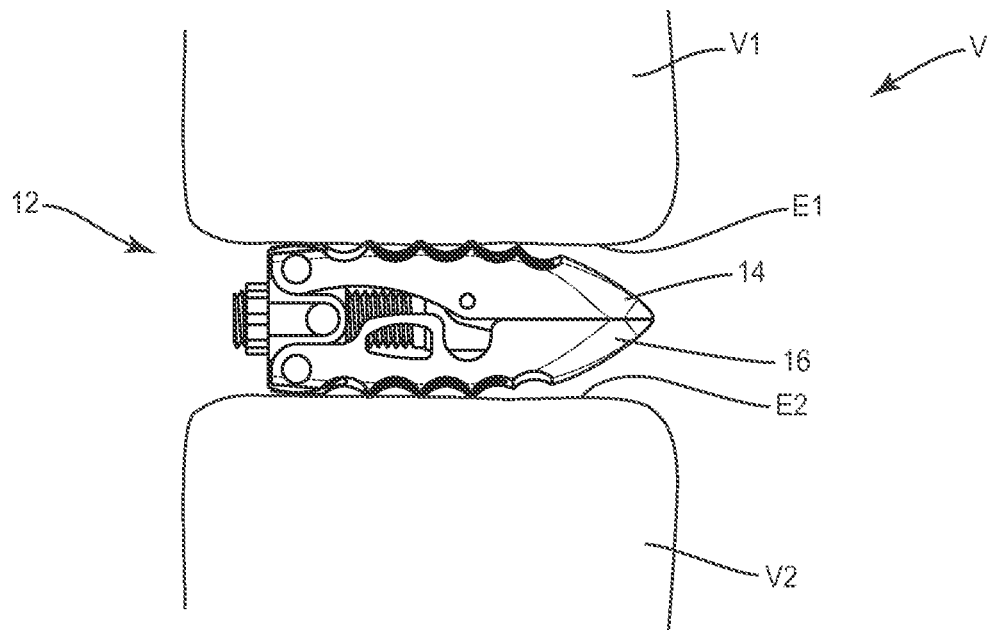
FIG. 5 is a side view of components of one embodiment of a spinal implant system in accordance with the principles of the present disclosure disposed with vertebrae.
Figure 6:
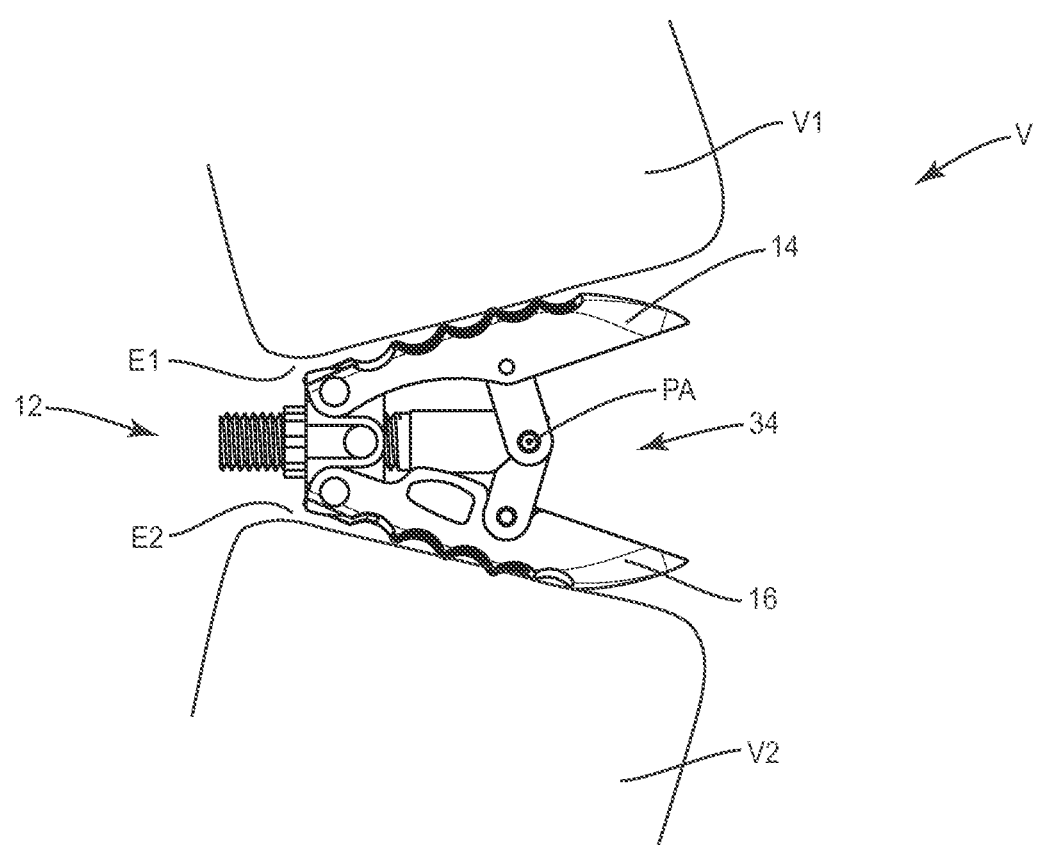
FIG. 6 is a side view of components of one embodiment of a spinal implant system in accordance with the principles of the present disclosure disposed with vertebrae.
Figure 7:
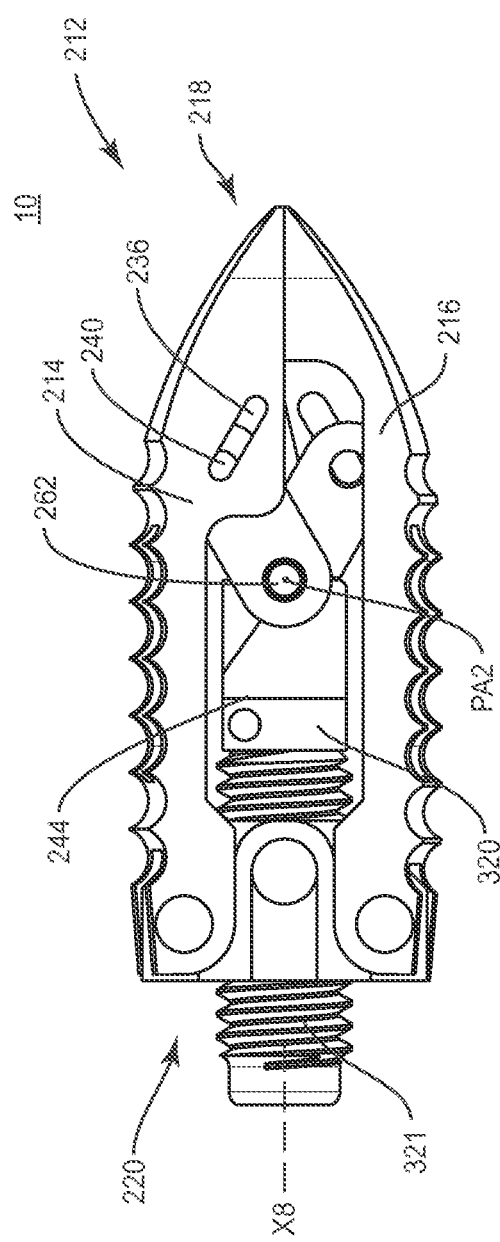
FIG. 7 is a side view of components of one embodiment of a spinal implant system in accordance with the principles of the present disclosure.
Figure 9:
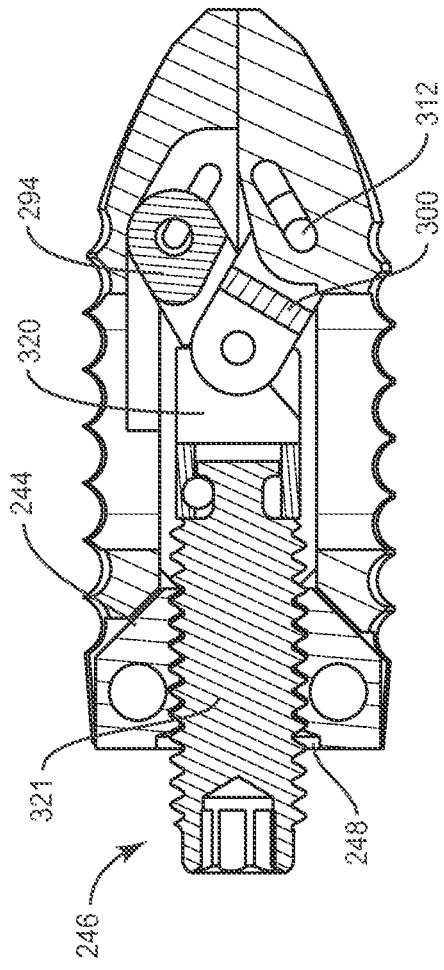
FIG. 9 is a cross section view of the components shown in FIG. 8 taken along lines A-A.
Figure 8:
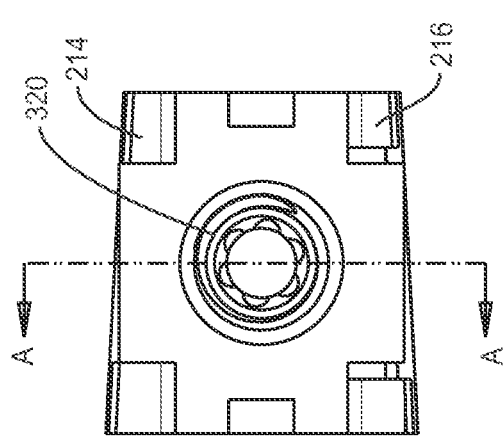
FIG. 8 is an end view of the components shown in FIG. 7.
Figure 10:
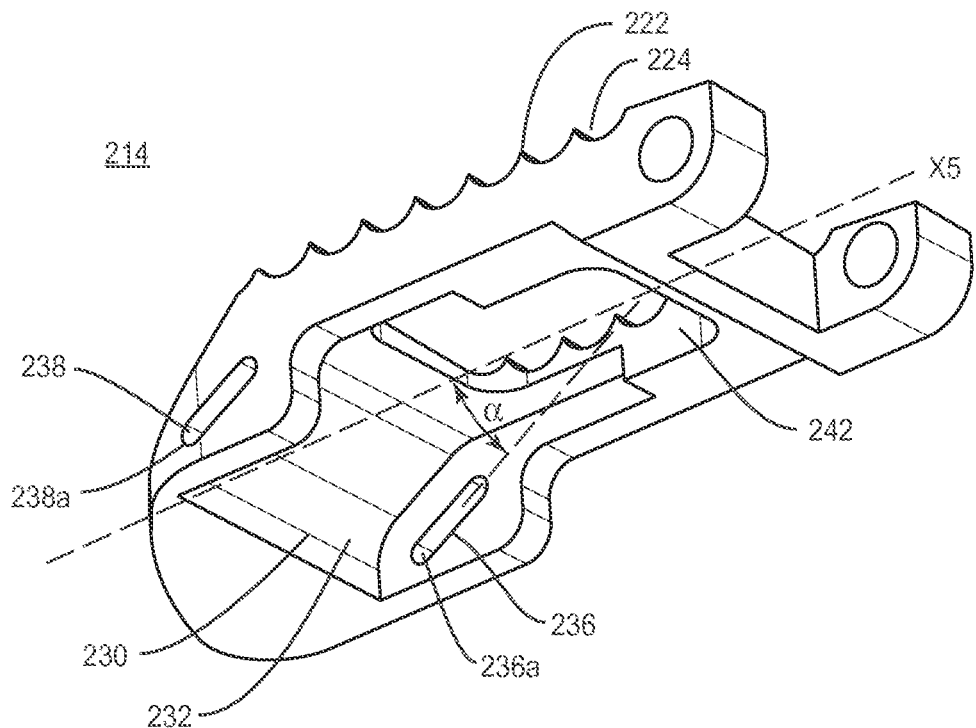
FIG. 10 is a perspective view of components of one embodiment of a spinal implant system in accordance with the principles of the present disclosure.
Figure 11:
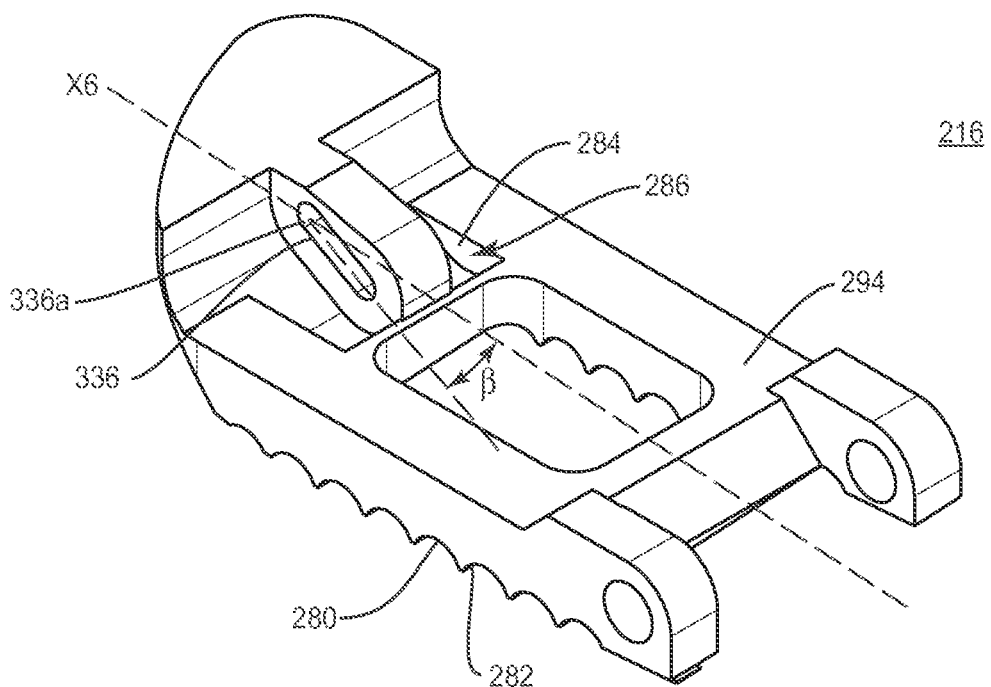
FIG. 11 is a perspective view of components of one embodiment of a spinal implant system in accordance with the principles of the present disclosure.

In assembly, operation and use, as shown in FIGS. 5 and 6, spinal implant system 10, similar to the systems and methods described herein, includes interbody implant 12 described herein and is employed with a surgical procedure for treatment of a spine of a patient including vertebrae V. Spinal implant system 10 may also be employed with surgical procedures, such as, for example, discectomy, laminectomy, fusion, laminotomy, laminectomy, nerve root retraction, foramenotomy, facetectomy, decompression, spinal nucleus or disc replacement.

Spinal implant system 10 is employed with a lumbar interbody fusion including surgical arthrodesis to immobilize a joint for treatment of an applicable condition or injury of an affected section of a spinal column and adjacent areas within a body. For example, vertebrae V includes a vertebra V1 and a vertebra V2. In some embodiments, vertebrae V1, V2 include diseased and/or damaged vertebra and intervertebral discs. In some embodiments, components of spinal implant system 10 are configured for insertion with a vertebral space between vertebrae V1, V2 to space apart articular joint surfaces, provide support and maximize stabilization of vertebrae V.

In use, to treat the affected section of vertebrae V, a medical practitioner obtains access to a surgical site including vertebrae V in any appropriate manner, such as through incision and retraction of tissues. In some embodiments, spinal implant system 10 may be used in any existing surgical method or technique including open surgery, mini-open surgery, minimally invasive surgery and percutaneous surgical implantation, whereby vertebrae V is accessed through a mini-incision, or sleeve that provides a protected passageway and/or surgical pathway to the area. Once access to the surgical site is obtained, a surgical procedure, as described herein, is performed for treating the spine disorder. The diseased and/or damaged portion of vertebrae V, which may include diseased and/or damaged intervertebral discs, are removed to create a vertebral space between vertebrae V1, V2.

A preparation instrument (not shown) is employed to remove disc tissue, fluids, adjacent tissues and/or bone, and scrape and/or remove tissue from endplate surfaces E1 of vertebra V1 and/or endplate surface E2 of vertebra V2. In some embodiments, the size of interbody implant 12 is selected after trialing. In some embodiments, interbody implant 12 is visualized by fluoroscopy and oriented before introduction into the vertebral space.

Interbody implant 12 is provided in a contracted configuration, as shown for example in FIG. 1, and axes X2, X3 and X4 are disposed in parallel alignment. A surgical instrument such as, for example, an inserter including a driver is connected with interbody implant 12 for disposal in an introduction or delivery orientation, Interbody implant 12 is delivered to the surgical site, as shown in FIG. 5, for alignment of interbody implant 12 with the surgical pathway such that interbody implant 12 is disposed with the vertebral space between vertebrae V1, V2.

Interbody implant 12 is selectively expanded to treat a spinal disorder and provide stability to vertebrae V, as described herein. Nut 46 is rotated in a clockwise direction such that screw 121 translates in an axial direction, as shown by arrow B in FIG. 4, relative to housing 44, as described herein. Translation of screw 121 translates screw housing 120 and pivot axis PA, in the direction shown by arrow B, to draw linkage 34 in the axial direction to relatively rotate links 99, 100 about pivot axis PA, as shown by arrows E in FIG. 4. As links 99, 100 pivot about pivot axis PA, link 99 pivots about pin 40 and link 100 pivots about pin 62, causing members 14, 16 to expand, as shown in FIG. 6.

In some embodiments, the configuration of interbody implant 12, and/or the expanded or contracted configuration of interbody implant 12, can be modified or adjusted via expansion or contraction of members 14, 16, as described herein, such that interbody implant 12 is adjustable, which may include prior to implantation or in situ. In some embodiments, interbody implant 12 provides a footprint that improves stability and decreases the risk of subsidence into tissue. In some embodiments, interbody implant 12 provides height restoration between vertebral bodies, lordosis, decompression, restoration of sagittal and/or coronal balance and/or resistance of subsidence into vertebral endplates.

In some embodiments, interbody implant 12 engages and spaces apart opposing endplate surfaces E1, E2 and is secured within a vertebral space to stabilize and immobilize portions of vertebrae V in connection with bone growth for fusion and fixation of vertebrae V1, V2. Fixation of interbody implant 12 with endplate surfaces E1, E2 may be facilitated by the resistance provided by the joint space and/or engagement with endplate surfaces E1, E2.

In some embodiments, interbody implant 12 may engage only one endplate. Components of spinal implant system 10 including interbody implant 12 can be delivered or implanted as a pre-assembled device or can be assembled in situ. Components of spinal implant system 10 including interbody implant 12 may be completely or partially revised, removed or replaced in situ. In some embodiments, one or all of the components of spinal implant system 10 can be delivered to the surgical site via mechanical manipulation and/or a free hand technique.

In one embodiment, spinal implant system 10 includes a plurality of interbody implants 12. In some embodiments, employing a plurality of interbody implants 12 can optimize the amount of vertebral space that can be spaced apart such that the joint spacing dimension can be preselected. The plurality of interbody implants 12 can be oriented in a side by side engagement, spaced apart and/or staggered.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of interbody implant 12 with vertebrae. In some embodiments, the agent may include one or a plurality of therapeutic agents and/or pharmacological agents for release, including sustained release, to treat, for example, pain, inflammation and degeneration.

In some embodiments, interbody implant 12 may include fastening elements, which may include locking structure, configured for fixation with vertebrae V1, V2 to secure joint surfaces and provide complementary stabilization and immobilization to a vertebral region. In some embodiments, locking structure may include fastening elements, such as, for example, bone fasteners, rods, plates, clips, hooks, adhesives and/or flanges. In some embodiments, the components of spinal implant system 10 can be used with screws to enhance fixation. The components of spinal implant system 10 can be made of radiolucent materials such as polymers. Radiomarkers may be included for identification under x-ray, fluoroscopy, CT or other imaging techniques.

In some embodiments, the use of microsurgical and image guided technologies may be employed to access, view and repair spinal deterioration or damage, with the aid of spinal implant system 10. Upon completion of the procedure, the non-implanted components, surgical instruments and assemblies of spinal implant system 10 are removed and the incision is closed.

In one embodiment, as shown in FIGS. 7-16, spinal implant system 10, similar to the systems and methods described herein, includes an interbody implant 212, similar to interbody implant 12 described with regard to FIGS. 1-6. Interbody implant 212 includes a member 214 and a member 216. Interbody implant 212 extends between an end 218 and an end 220. Member 214 defines a longitudinal axis X5. Member 214 includes a surface 222 that defines a vertebral engaging surface 224. Member 214 and member 216 are connected by a linkage 234, as described herein. Member 214 includes a surface 230 that defines a cavity 232 configured for disposal of a portion of linkage 234, as described herein. Surface 230 defines a slot 236 and a slot 238 disposed contra-lateral to slot 236. Slots 236, 238 are each disposed at an angle α relative to axis X5.

Figure 12:
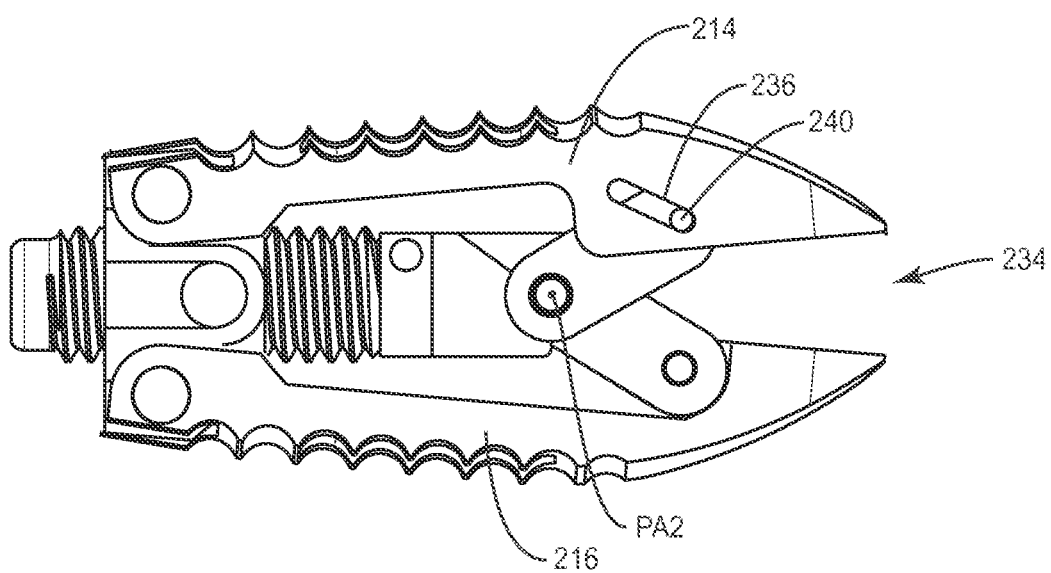
FIG. 12 is a side view of the components shown in FIG. 7.
Figure 13:
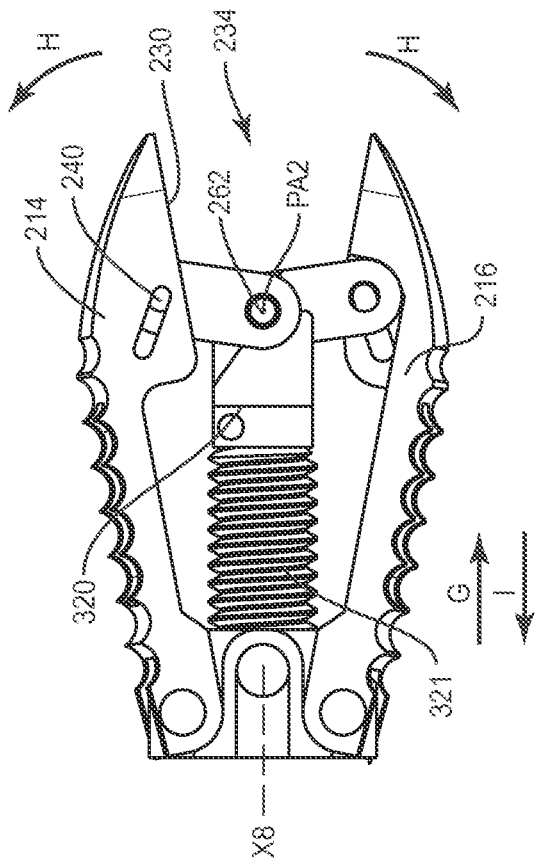
FIG. 13 is a side view of the components shown in FIG. 7.
Figure 15:
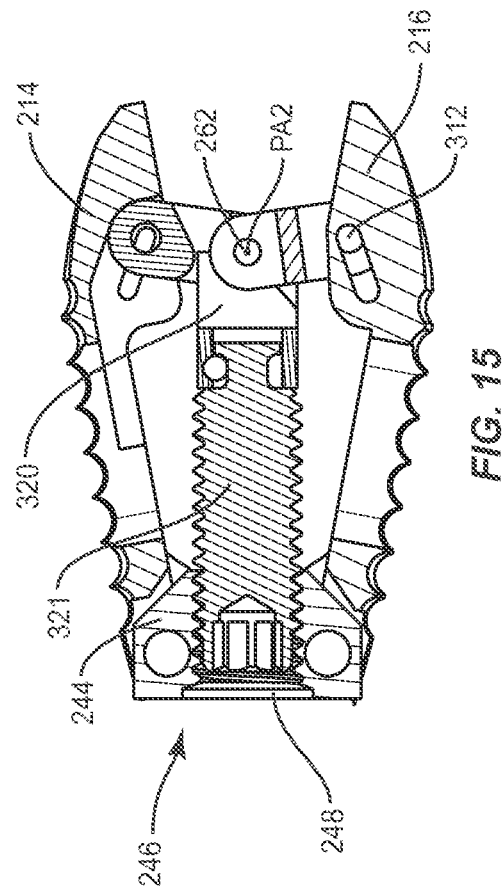
FIG. 15 is a cross section view of the components shown in FIG. 14 taken along lines B-B.
Figure 14:
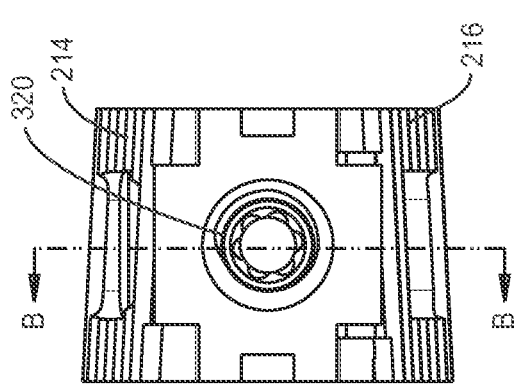
FIG. 14 is an end view of the components shown in FIG. 7.
Figure 16:
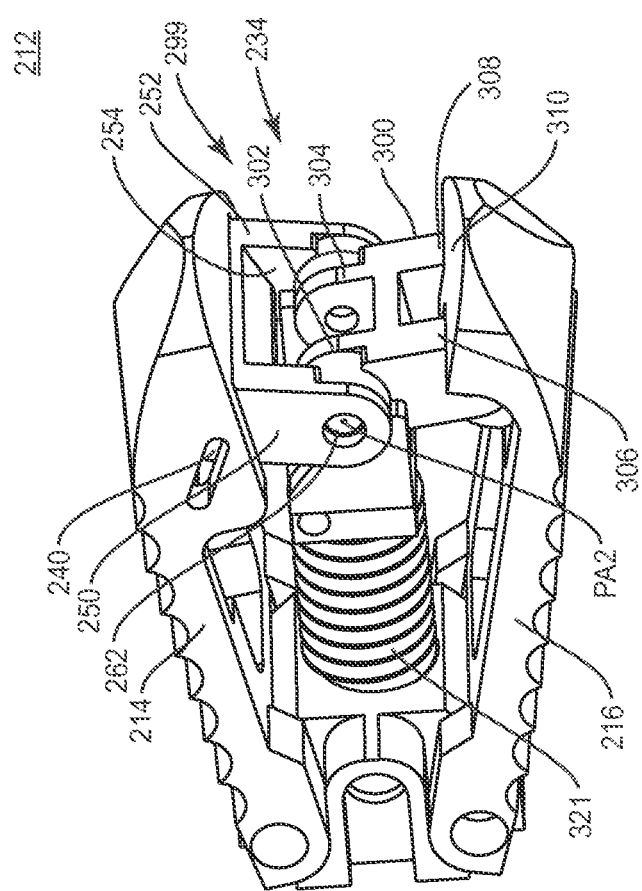
FIG. 16 is a perspective view of the components shown in FIG. 7.

Slots 236, 238 are configured for disposal of a connecting element, such, as for example, a pin 240, as described herein. As pin 240 translates within and relative to slots 236, 238, member 214 expands in a first or initial zone of expansion of interbody implant 212. The first expansion zone includes an initial, first or selected amount of expansion, separation and/or spacing apart of members 214, 216 such that interbody implant 212 has an initial, first or selected height, as shown in FIG. 12. Slots 236, 238 each include a ramp configuration to facilitate expansion of members 214, 216 in the first expansion zone. As pin 240 engages end points 236*a*, 238*a* of slots 236, 238, pin 240 rotates relative to slots 236, 238 such that members 214 can expand in a second zone of expansion via linkage 234, as described herein. The second expansion zone includes a second or selected amount of expansion, separation and/or spacing apart of members 214, 216 in addition to or separate from the first expansion zone such that interbody implant 212 has a final, second or selected height, as shown in FIG. 13. In some embodiments, this configuration of interbody implant 212 allows for increased expansion height of interbody implant 212 and/or allows for disposal of linkage 234 at a minimum initial angle, as described herein.

Surface 230 defines a cavity 242. Cavity 242 is in communication with a cavity 294 of member 216, as described herein. Cavities 242, 294 are configured for disposal of a body, such as, for example, a housing 244, as described herein. Housing 244 is configured to connect member 214 with member 216. Housing 244 and cavities 242, 294 are configured for moveable disposal of an actuator 246, as described herein. Housing 244 and cavities 242, 294 are configured for rotatable disposal of actuator 246, as described herein. An opening 248 is disposed at end 220 and is in communication with cavity 242. Opening 248 is configured for disposal of a portion of actuator 246, as described herein.

Linkage 234, similar to linkage 34, includes one or a plurality of links. Linkage 234 has a link 299, which includes an arm 250 and an arm 252. Arm 252 is spaced apart in relation to arm 250 to define a cavity 254. Cavity 254 is configured for disposal of a complimentary link 300. Link 300 is configured for movable disposal between arms 250, 252. Arms 250, 252 are configured for engagement with pin 240. Arms 250, 252 are configured for engagement with a pin 262, as described herein. Pin 262 is configured to connect linkage 234 with actuator 246 at a pivot axis PA2. Pivot axis PA2 is disposed transverse to an axis of actuator 246, as described herein. Pin 262 is connected with actuator 246 to actuate expansion of members 214, 216, as described herein.

In some embodiments, arms 250, 252 are configured with equal lengths. In some embodiments, arm 250 includes a length greater than arm 252. In some embodiments, arm 250 includes a length less than a length of arm 252.

Member 216 defines a longitudinal axis X6. Member 216 includes a surface 280 that defines a vertebral engaging surface 282. Member 216 includes a surface 284 that defines a cavity 286 configured for a portion of linkage 234, such as, for example, link 300. Link 300 includes a substantially H-shape and includes an arm 302, an arm 304, an arm 306 and an arm 308. Arm 302 is spaced apart in relation to arm 304. Arms 302, 304 are configured for disposal of pin 262. Link 300 is configured to pivot relative to arms 250, 252 about pin 262 to expand and contract interbody implant 212.

Arm 306 is spaced apart in relation to arm 308. Arms 306, 308 define a cavity 310 configured for disposal of a pin 312. Pin 312 is configured to facilitate rotation of link 300 relative to member 216 about pin 312. Each arm 302, 304, 306, 308 may have a variety of shapes and configurations.

A slot 336 is configured for disposal of pin 312. Slot 336 is disposed in cavity 284. Slot 336 is disposed at an angle 3 relative to axis X6. As pin 312 translates relative to slot 336, member 216 expands in the first expansion zone along slot 336. Slot 336 is configured as a ramp to facilitate expansion of member 216 in the first expansion zone. As pin 312 engages an end point 336*a* of slot 336, pin 312 rotates relative to slot 336 causing member 216 to expand in the second expansion zone via linkage 234.

In some embodiments, the first expansion zone and the second expansion zone include different rates of expansion. In some embodiments, the first expansion zone and/or the second expansion zone include one or a plurality of rates of expansion. In some embodiments, the first expansion zone and the second expansion zone include the same rate of expansion. In some embodiments, interbody implant 212 has a uniform or linear expansion rate for the first expansion zone. In some embodiments, interbody implant 212 has a variable expansion rate for the first expansion zone. In some embodiments, interbody implant 212 has a uniform or linear expansion rate for the second expansion zone.

Figure 17:
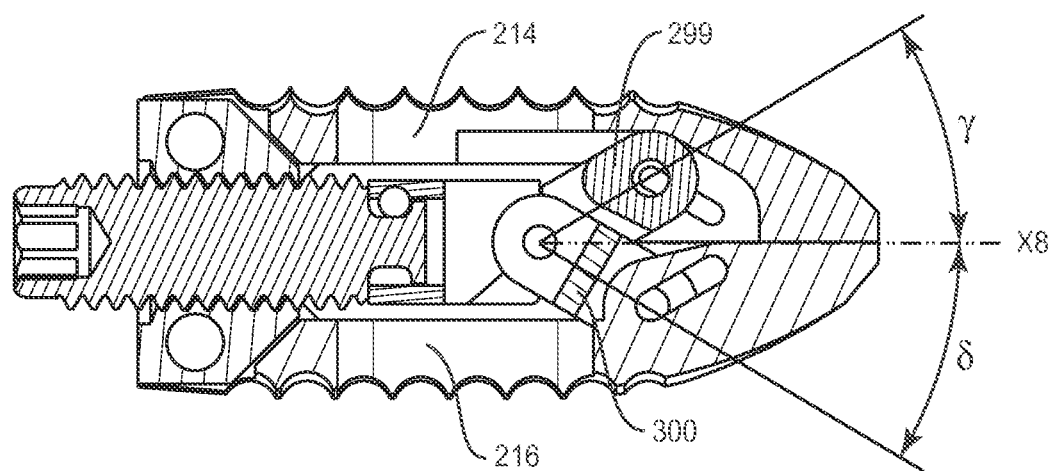
FIG. 17 is a side view of components of one embodiment of a spinal implant system in accordance with the principles of the present disclosure.
Figure 18:
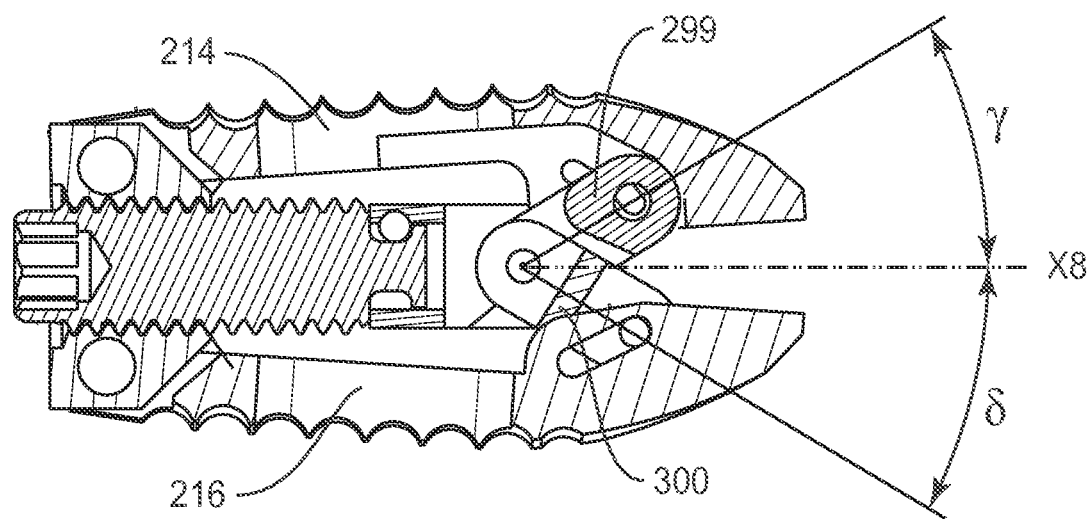
FIG. 18 is a side view of components of one embodiment of a spinal implant system in accordance with the principles of the present disclosure.
Figure 22:
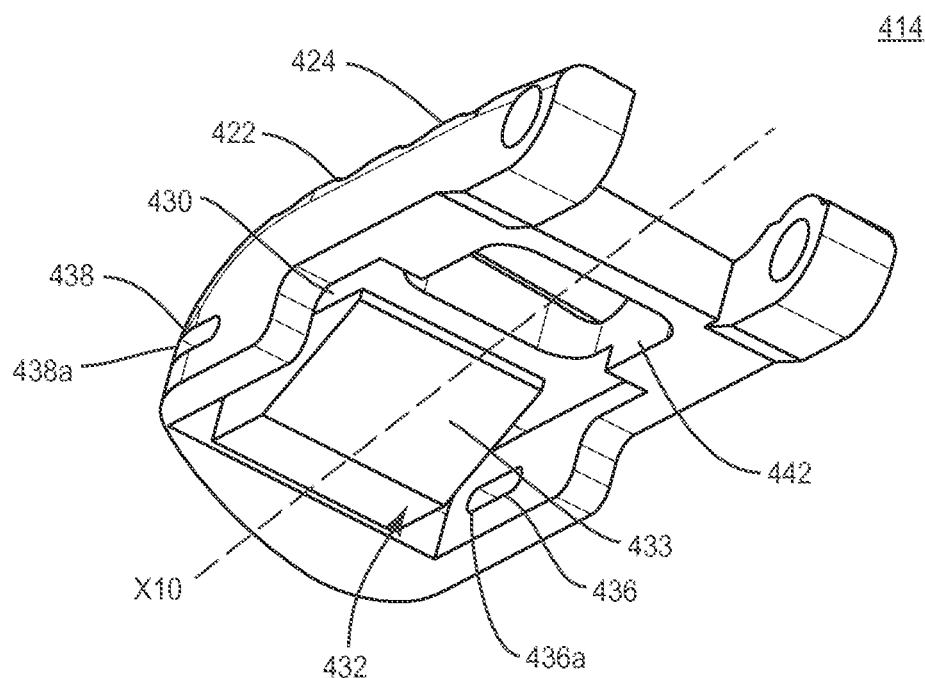
FIG. 22 is a perspective view of components of one embodiment of a spinal implant system in accordance with the principles of the present disclosure.

In some embodiments, links 299, 300 are relatively disposed at a minimum angle. In some embodiments, link 299 is disposed at an angle γ relative to axis X8 and link 300 is disposed at an angle δ relative to axis X8, as shown in FIG. 17. In some embodiments, links 299, 300 are relatively disposed at a minimum angle and/or no less than an angle of 20 degrees. In some embodiments, links 299, 300 are relatively disposed at a minimum angle and/or no less than an angle of 20 degrees when interbody implant 212 is bearing load, as described herein. In some embodiments, links 299, 300 are relatively disposed at an angle in a range of greater than 20 degrees. In some embodiments, the minimum angle provides a reduction of stresses in one or more components of interbody implant 212. In some embodiments, links 299, 300 are relatively disposed at an angle that remains constant in the first expansion zone, as shown in FIG. 18.

Surface 284 defines cavity 294. Cavity 294 is configured for disposal of housing 244 and actuator 246, as described herein. Actuator 246 includes a screw housing 320 and a screw 321 threadingly engaged therewith. Screw housing 320 and shaft 321 define an axis X8. Axis X8 extends parallel to axes X5, X6 when interbody implant 212 is in a contracted configuration. Screw housing 320 is connected with pin 262 at pivot axis PA2. Pivot axis PA2 is disposed transverse to axis X8.

Actuator 246 is engaged with a surgical instrument, such as, for example, a driver (not shown). The driver engages and rotates screw 321. Screw 321 is threaded with, and rotates relative to and within housing 244 such that screw 321 translates relative to housing 244. Screw 321 is threaded with, and rotates relative to and within screw housing 320 such that screw 321 remains axially fixed with screw housing 320 to translate and/or drive pin 262 and pivot axis PA2 axially. Axial translation of pivot axis PA2 relatively rotates links 299, 300 to facilitate expansion and contraction of members 214, 216 about pivot axis PA2.

As screw 321 is rotated clockwise, screw 321 translates in a direction shown by arrow C in FIG. 12, relative to housing 244 via the threaded engagement within housing 244, Screw 321 translates relative to housing 244, in the direction shown by arrow G, such that screw housing 320 axially translates linkage 234. Pin 240 translates along slots 236, 238 and pin 312 translates along slot 336, as described herein. Translation of pins 240, 312 causes members 214, 216 to expand in the first expansion zone. Linkage 234 remains in a fixed and collapsed orientation during translation, as shown in FIG. 12. As pin 240 engages ends 236a, 238a, and pin 312 engages end 336a, linkage 234 expands causing members 214, 216 to expand in the second expansion zone.

Linkage 234 engages ends 236a, 238a and 336a. As such, linkage 234 expands causing arms 250, 252 and link 300 to rotate about pivot axis PA2, as shown by arrows H in FIG. 13. As links 299, 300 pivot about pivot axis PA2, link 299 pivots about pin 240 and link 300 pivots about pin 312 causing members 214, 216 to expand in the second expansion zone. Translation of screw 321 relative to housing 244, in a direction shown by arrow I in FIG. 13, translates screw housing 320 and draws links 299, 300 in an axial direction causing links 299, 300 to pivot about pivot axis PA2 causing members 214, 216 to contract. In some embodiments, the embodiments of an interbody implant described herein can include an actuator having a rotating nut and a fixed threaded shaft, similar to that described with regard to FIGS. 1-5. In some embodiments, the embodiments of an interbody implant described herein can include an actuator having a rotating threaded shaft and a fixed threaded housing, similar to that described with regard to FIGS. 6-28.

In one embodiment, as shown in FIGS. 19-27, spinal implant system 10, similar to the systems and methods described herein, includes an interbody implant 412, similar to interbody implant 12 described herein.

Interbody implant 412 includes a member 414 and a member 416. Interbody implant 412 extends between an end 418 and an end 420. Member 414 defines a longitudinal axis X10. Member 414 includes a surface 422 that defines a vertebral engaging surface 424. Member 414 and member 416 are connected by a linkage 434, as described herein. Member 414 includes a surface 430 that defines a cavity 432 configured for disposal of a portion of linkage 434, as described herein. Surface 430 defines a dynamic slot 436 and a dynamic slot 438 disposed contralateral to slot 436. Slots 436, 438 are in alignment with axis X10. Surface 430 defines a ramp 433. Ramp 433 is configured for engagement with a protrusion 501 disposed with link 500, as described herein.

Slots 436, 438 are configured for disposal of a pin 440, as described herein. As pin 440 translates relative to slots 436, 438, member 414 expands in a first expansion zone. As pin 440 engages an end point 436a, 438a of slots 436, 438, pin 440 rotates relative to slots 436, 438 and causes member 414 to expand in a second expansion zone.

Surface 430 defines a cavity 442. Cavity 442 is in communication with a cavity 494 of member 416, as described herein. Cavities 442, 494 are configured for disposal of a housing 444, as described herein. Housing 444 is configured to connect member 414 with member 416. Housing 444 and cavities 442, 494 are configured for moveable disposal of an actuator 446, as described herein. Housing 444 and cavities 442, 494 are configured for rotatable disposal of actuator 446, as described herein. An opening 448 is disposed at end 420 and is in communication with cavity 442. Opening 448 is configured for disposal of a portion of actuator 446, as described herein.

Linkage 434, similar to linkage 34, includes a link 499, which includes an arm 450 and an arm 452. Arm 452 is spaced apart in relation to arm 450 to define a cavity 454. Cavity 454 is configured for disposal of a complimentary link 500. Link 500 is configured for movable disposal between arms 450, 452. Arms 450, 452 are configured for engagement with pin 440. Arms 450, 452 are configured for engagement with a pin 462, as described herein. Pin 462 is configured to connect linkage 434 with actuator 446 at a pivot axis PA3. Pivot axis PA3 is disposed transverse to an axis of actuator 446, as described herein. Pin 462 is connected with actuator 446 to actuate expansion of members 414, 416, as described herein. Arms 450, 452 each include a protrusion 470, 472. Protrusions 470, 472 engage ramps 490, 492 to facilitate expansion of member 414 in a first expansion zone, similar to that described herein. Protrusions 470, 472 are configured as load bearing surfaces while member 416 expands in the first expansion zone.

Figure 23:
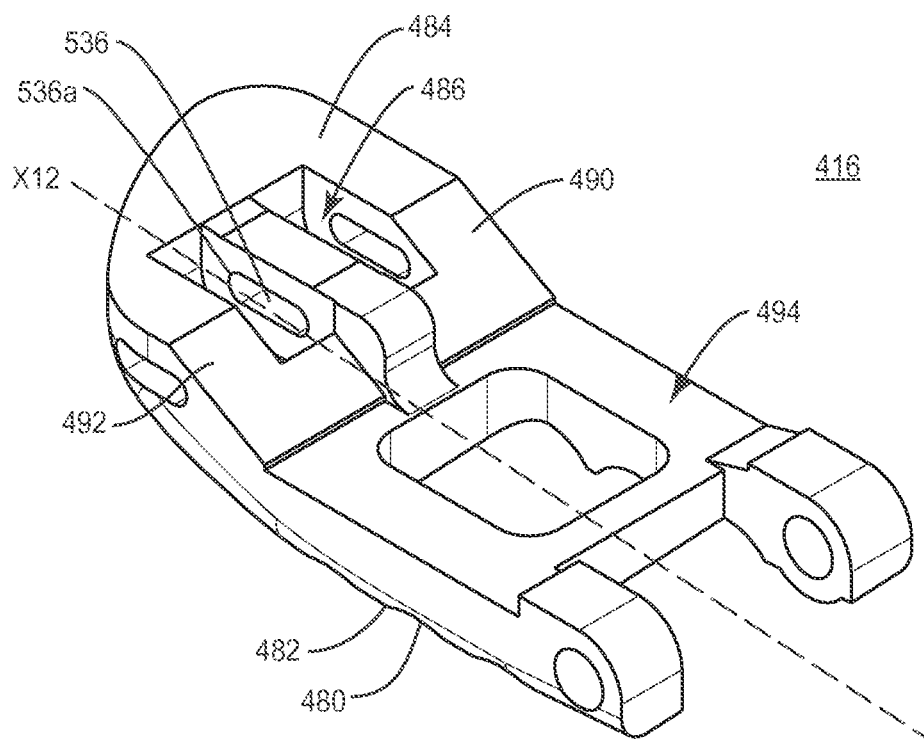
FIG. 23 is a perspective view of components of one embodiment of a spinal implant system in accordance with the principles of the present disclosure.

Member 416 defines a longitudinal axis X12. Member 416 includes a surface 480 that defines a vertebral engaging surface 482. Member 416 includes a surface 484 that defines a cavity 486 configured for a portion of linkage 434, such as, for example, link 500. Surface 484 defines ramp 490 and ramp 492. As shown in FIG. 23, ramps 490, 492 include an angle of inclination oriented transverse relative to axis X12.

As protrusions 470, 472 translate along ramps 490, 492, linkage 434 expands causing members 414, 416 to expand in the first expansion zone.

Link 500 is substantially H-shaped and includes an arm 502, an arm 504, an arm 506 and an arm 508. Arm 502 is spaced apart in relation to arm 504. Arms 502, 504 are configured for disposal of pin 462. Link 500 is configured to pivot relative to arms 450, 452 about pin 462 to expand and contract interbody implant 412. Arm 506 is spaced apart in relation to arm 508. Arms 506, 508 define a cavity 510 configured for disposal of a pin 512. Pin 512 is configured to facilitate rotation of link 500 relative to member 416 about pin 512. Protrusion 501 is configured for engagement with ramp 433. Protrusion 501 is configured as a load bearing surface as member 14 expands in the first expansion zone.

A slot 536 is configured for disposal of pin 512. Slot 536 is generally co-axial with axis X12. As pin 512 translates relative to slot 536, linkage 434 and member 416 expand in the first expansion zone along slot 536, similar to that described herein. As pin 512 engages an end point 536a of slot 536, pin 512 rotates relative to slot 536 causing linkage 434 and member 416 to expand in a second expansion zone, similar to that described herein.

Figure 28:
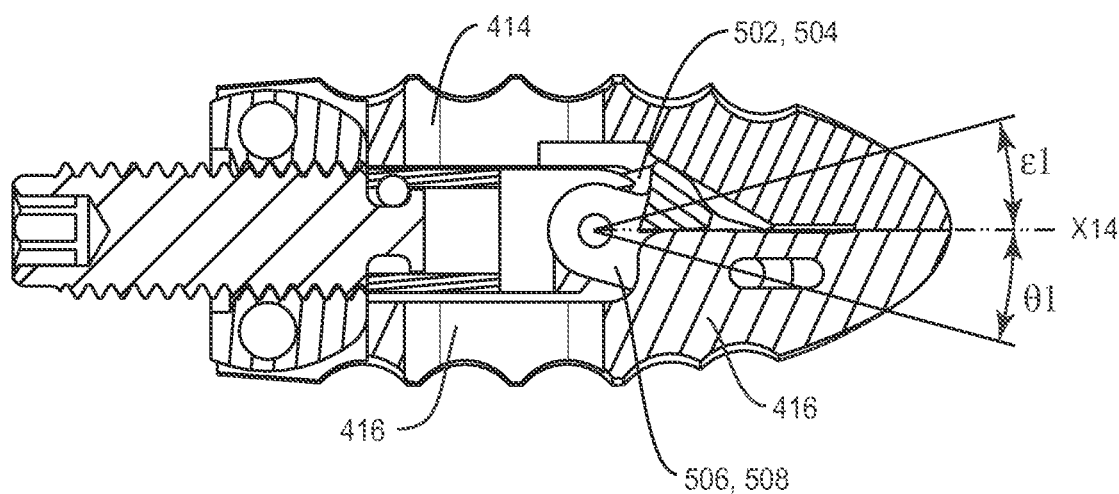
FIG. 28 is a side view of components of one embodiment of a spinal implant system in accordance with the principles of the present disclosure.
Figure 29:
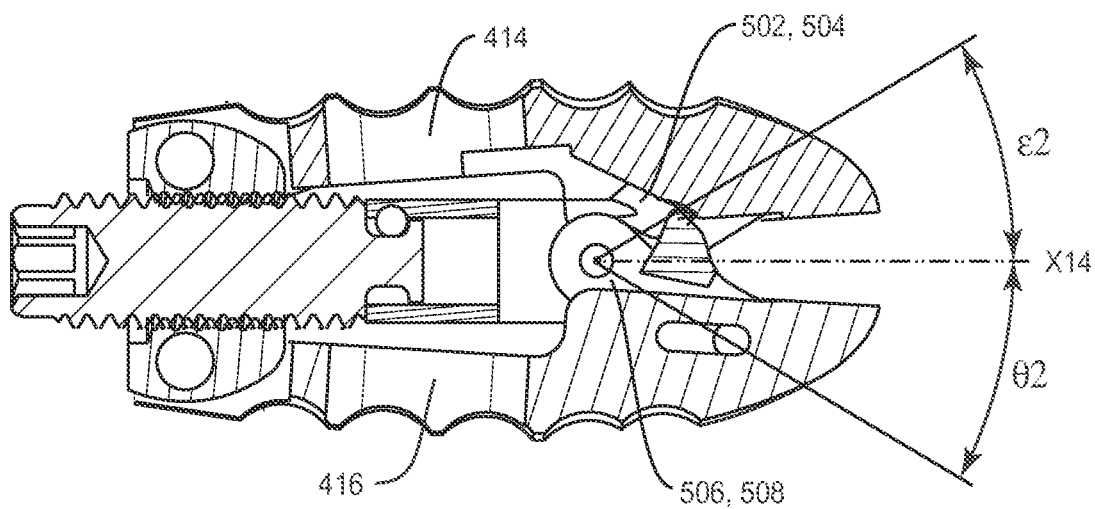
FIG. 29 is a side view of components of one embodiment of a spinal implant system in accordance with the principles of the present disclosure.
Figure 30:
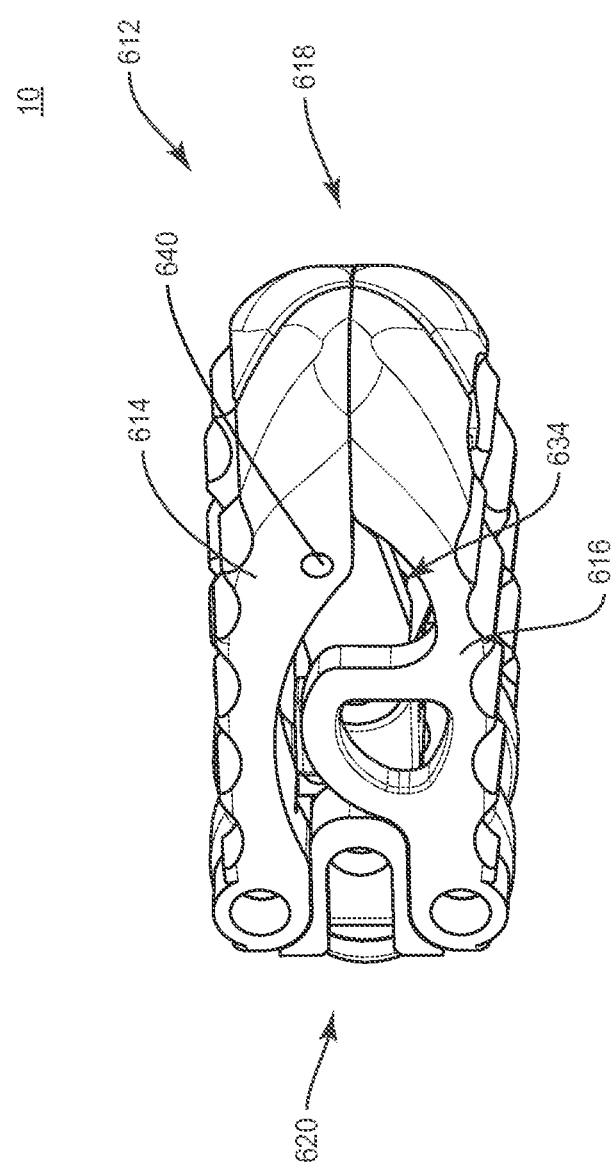
FIG. 30 is a perspective view of components of one embodiment of a spinal implant system in accordance with the principles of the present disclosure.
Figure 31:
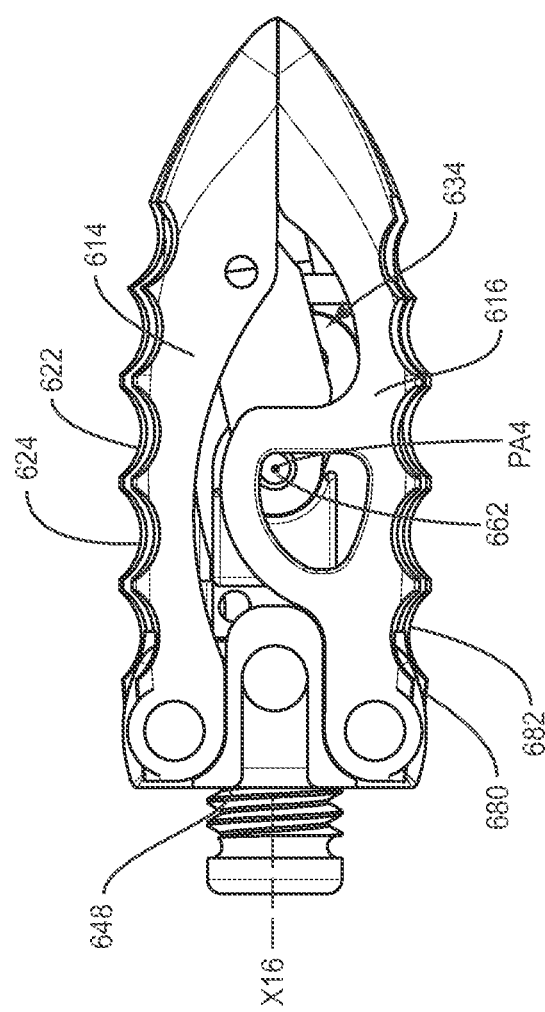
FIG. 31 is a side view of the components shown in FIG. 30.
Figure 32:
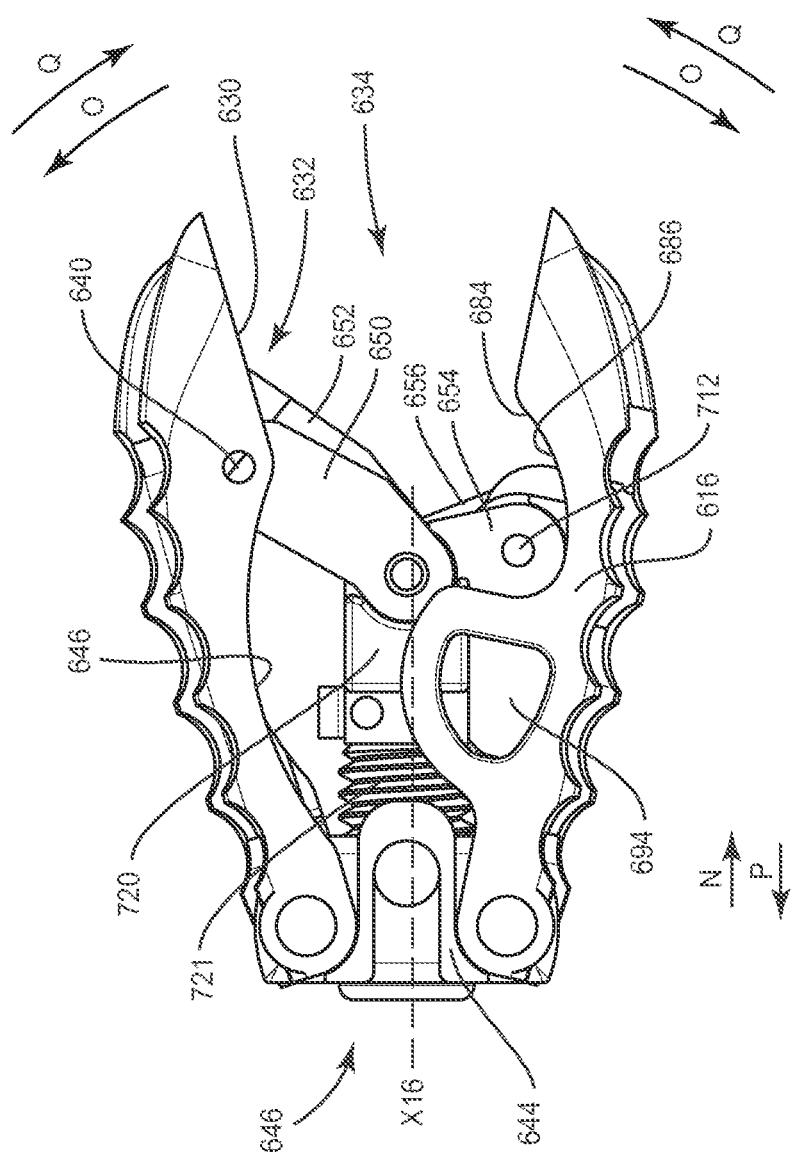
FIG. 32 is a side view of the components shown in FIG. 30.
Figure 33:
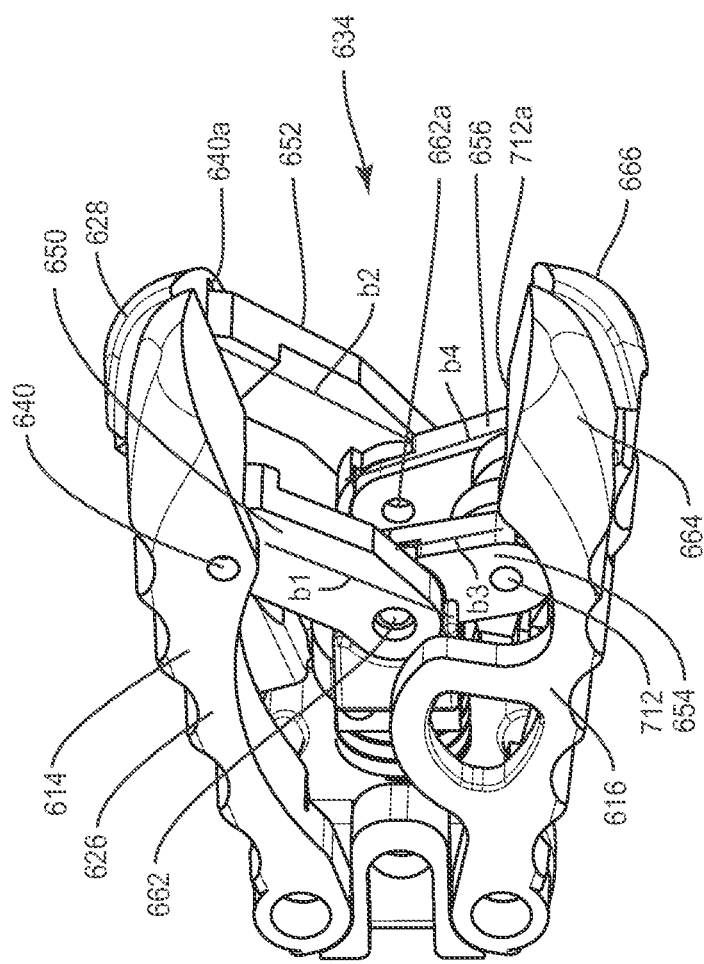
FIG. 33 is a perspective view of the components shown in FIG. 30.

In some embodiments, arms 502, 504 are disposed relative to arms 506, 508 at a minimum angle. In some embodiments, arms 502, 504 are disposed at an angle ε1 relative to axis X14 and arms 506, 508 are disposed at an angle θ1 relative to axis X14, as shown in FIG. 28. In some embodiments, arms 502, 504 and arms 506, 508 are relatively disposed at a minimum angle and/or no less than an angle of 20 degrees. In some embodiments, arms 502, 504 and arms 506, 508 are relatively disposed at a minimum angle and/or no less than an angle of 20 degrees when interbody implant 412 is bearing load, as described herein. In some embodiments, arms 502, 504 and arms 506, 508 are relatively disposed at an angle in a range of greater than 20 degrees. In some embodiments, the minimum angle provides a reduction of stresses in one or more components of interbody implant 412. In some embodiments, arms 502, 504 and arms 506, 508 are relatively disposed at an angle that increases in the first expansion zone, such that arms 502, 504 are disposed at an angle ε2 relative to axis X14 and arms 506, 508 are disposed at an angle θ2 relative to axis X14, as shown in FIG. 29.

Surface 484 defines cavity 494. Cavity 494 is configured for disposal of housing 444 and actuator 446, as described herein. Actuator 446 includes a screw housing 520 and a screw 521 threadingly engaged therewith. Screw housing 520 and screw 521 define an axis X14. Axis X14 extends generally parallel to axes X10, X12 when interbody implant 412 is in a contracted configuration. Screw housing 520 and screw 521 are connected with pin 462 at pivot axis PA3. As shown in FIGS. 19 and 24, pivot axis PA3 is disposed transverse to axis X14.

Actuator 446 is engaged with a surgical instrument, such as, for example, a driver (not shown), The driver engages and rotates screw 521, Screw 521 is threaded with, and rotates relative to and within housing 444 such that screw 521 translates relative to housing 444. Screw 521 is threaded with, and rotates relative to and within screw housing 520 such that screw 521 remains axially fixed with screw housing 520 to translate and/or drive pin 462 and pivot axis PA3 axially. Axial translation of pivot axis PA3 relatively rotates links 499, 500 to facilitate expansion and contraction of members 414, 416 about pivot axis PA3.

For example, as screw 521 is rotated clockwise, screw 521 translates, in a direction shown by arrow K in FIG. 24, relative to housing 444 via the threaded engagement within housing 444. Translation of screw 521 translates screw housing 520 and linkage 434 causing pin 440 to translate along slots 436, 438 and pin 512 to translate along slot 536. Translation of linkage 434 causes members 414, 416 to expand in the first expansion zone. As pin 440 engages ends 436a, 438a and pin 512 engages end 536a, linkage 434 and members 514, 516 expand in the second expansion zone.

As screw 521 translates linkage 434 along slots 436, 438 and 536, protrusions 470, 472 translate along ramps 490, 492. Protrusions 470, 472 and ramps 490, 492 provide a load bearing interface to prevent the force from being applied to linkage 434 during the first expansion zone. As linkage 434 engages ends 436a, 438a and 536a, linkage 434 expands causing links 499, 500 to rotate about pivot axis PA3, as shown by arrows L in FIG. 24, As links 499, 500 rotate about pivot axis PA3, link 499 pivots about pin 440 and link 500 pivots about pin 512 causing members 414, 416 to expand in the second expansion zone. Relative translation of screw 521, in a direction shown by arrow M in FIG. 24, translates screw housing 520 and draws links 499, 500 axially causing links 499, 500 to pivot about pivot axis PA3 causing members 414, 416 to contract.

In one embodiment, as shown in FIGS. 30-33, spinal implant system 10, similar to the systems and methods described herein, includes an interbody implant 612, similar to interbody implant 12 described herein.

Interbody implant 612 includes a member 614 and a member 616. Interbody implant 612 extends between an end 618 and an end 620. Member 614 includes a surface 622 that defines a vertebral engaging surface 624. Member 614 includes a portion 626 and a portion 628. Portions 626, 628 are configured to engage vertebrae at various angles to facilitate lordosis, as described herein.

Member 614 and member 616 are connected by a linkage 634, as described herein. Member 614 includes a surface 630 that defines a cavity 632 configured for disposal of a portion of linkage 634, as described herein. Surface 630 defines a cavity 642. Cavity 642 is in communication with a cavity 694 of member 616. Cavities 642, 694 are configured for disposal of a housing 644, as described herein. Housing 644 is configured to connect member 614 with member 616. Housing 644 and cavities 642, 694 are configured for moveable disposal of an actuator 646, as described herein. Housing 644 and cavities 642, 694 are configured for rotatable disposal of actuator 646, as described herein. An opening 648 is disposed at end 620 and is in communication with cavity 642. Opening 648 is configured for disposal of a portion of actuator 646, as described herein.

Linkage 634 includes a link 650, a link 652, a link 654 and a link 656. Links 650, 652 are configured for disposal with cavity 632. Link 650 is connected with portion 626 by a pin 640. Portion 626 is configured for relative rotation about pin 640 upon actuation of linkage 634, as described herein. Link 650 is configured for rotatable connection with link 654 by a pin 662. Pin 662 is configured to connect links 650, 654 with actuator 646 at a pivot axis PA4. Pivot axis PA4 is disposed transverse to an axis of actuator 646, as described herein. Pin 662 is connected with actuator 646 to actuate rotation of members 614, 616, as described herein.

Link 652 is connected with portion 628 by a pin 640a. Portion 628 is configured for relative rotation about pin 640a upon actuation of linkage 634, as described herein. Link 652 is configured for rotatable connection with arm 656 by a pin

662a. Pin 662a is configured to connect links 652, 656 with actuator 646 at pivot axis PA4. Pivot axis PA4 is disposed transverse to an axis of actuator 646, as described herein. Pin 662a is connected with actuator 646 to actuate rotation of portions 628, 666, as described herein.

Member 616 includes a surface 680 that defines a vertebral engaging surface 682. Member 616 includes a portion 664 and a portion 666. Portions 664, 666 are configured to engage vertebrae at various angles to facilitate lordosis, as described herein, Member 616 includes a surface 684 that defines a cavity 686 configured for disposal of links 654, 656.

Link 654 is connected with portion 664 by a pin 712. Portion 664 is configured for relative rotation about pin 712 upon actuation of linkage 634, as described herein. Link 654 is configured for rotatable connection with link 650 by pin 662, as described herein, Link 656 is connected with portion 666 by a pin 712a, Portion 666 is configured for relative rotation about pin 712a upon actuation of linkage 634, as described herein, Link 656 is configured for rotatable connection with link 652 by pin 662a, as described herein.

Each link 650, 652, 654, 656 may have a variety of shapes and configurations. Link 650 includes a length b1. Link 652 includes a length b2. Link 654 includes a length b3. Link 656 includes a length b4. The length of one or more of link 650, 652, 654 and 656 can be altered during manufacture for a specific lordotic angle for interbody implant 612 at expansion required by a surgical procedure, as shown in FIG. 28. In some embodiments, one or more of lengths b1, b2, b3 and b4 are different. In some embodiments, a non-equal length configuration facilitates adjustable spacing of vertebrae by interbody implant 612 to provide a variable lordotic implant.

Figure 27:
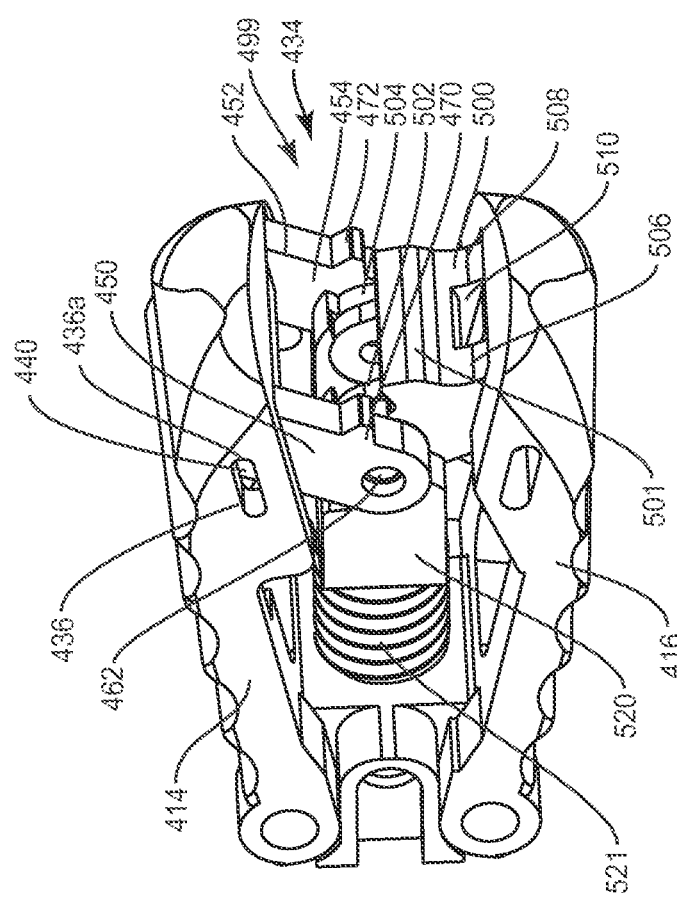
FIG. 27 is a perspective view of the components shown in FIG. 19.

Surface 684 defines cavity 694. Cavity 694 is configured for disposal of housing 644 and actuator 646, as described herein. Actuator 646 includes a screw housing 720 and a screw 721 threadingly engaged therewith. Screw housing 720 and screw 721 define an axis X16. Screw housing 720 and screw 721 are connected with pins 662, 662a at pivot axis PA4. As shown in FIGS. 26 and 27, pivot axis PA4 is disposed transverse to axis X16.

Actuator 646 is engaged with a surgical instrument, such as, for example, a driver (not shown). The driver engages and rotates screw 721. Screw 721 is threaded with, and rotates relative to and within housing 644 such that screw 721 translates relative to housing 644. Screw 721 is threaded with, and rotates relative to and within screw housing 720 such that screw 721 remains axially fixed with screw housing 720 to translate and/or drive pins 662, 662a and pivot axis PA4 axially. Axial translation of pivot axis PA4 relatively, rotates links 650, 652, 654, 656 to facilitate expansion and contraction of members 614, 616.

As screw 721 is rotated clockwise, screw 721 translates in a direction shown by arrow N in FIG. 27, relative to housing 644 via the threaded engagement within housing 644. Screw 721 axially translates screw housing 720 and linkage 634 causing links 650, 654 and links 652, 656 to rotate about pivot axis PA4, as shown by arrows O in FIG. 27. Differential lengths of links 650, 654 and links 652, 656 facilitate differential expansion of portions 626, 664 and portions 628, 666, respectively, to provide adjustable spacing of vertebrae by interbody implant 612 to provide a variable lordotic implant.

As screw 721 is rotated counter-clockwise, screw 721 translates, in a direction shown by arrow P in FIG. 27, relative to housing 644 via the threaded engagement within housing 644. Screw 721 axially translates screw housing 720 and linkage 634 causing links 650, 654 and links 652, 656 to rotate about pivot axis PA4, as shown by arrows Q in FIG. 27. Differential contraction of links 650, 654 and portions 626, 664, and links 652, 656 and portions 628, 666 facilitates adjustable spacing of vertebrae by interbody implant 612 to provide a variable lordotic implant.

Figure 34:
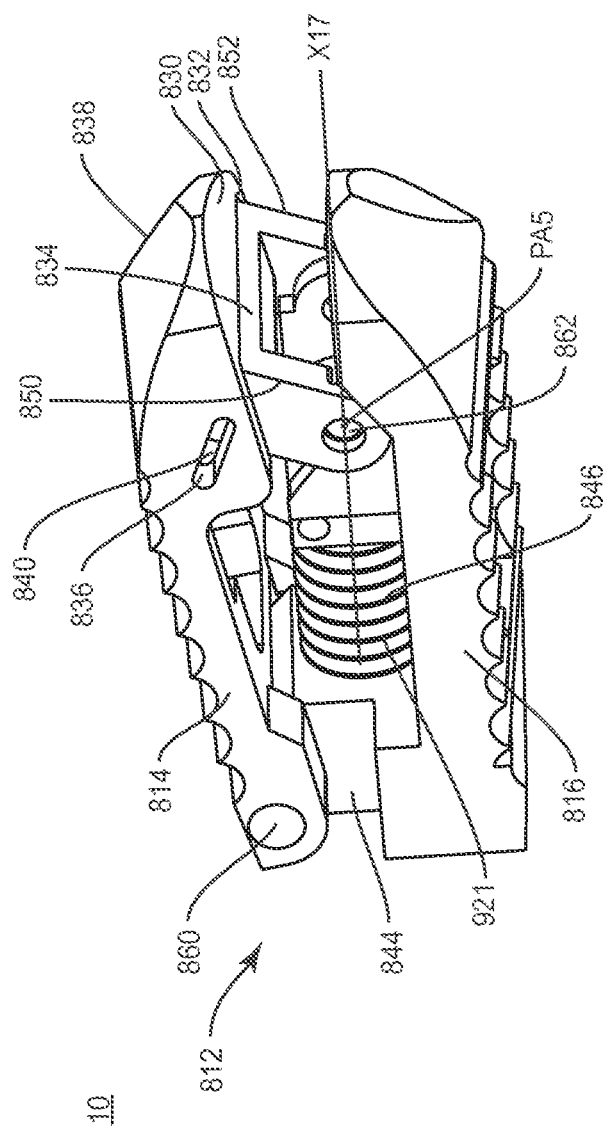
FIG. 34 is a perspective view of components of one embodiment of a spinal implant system in accordance with the principles of the present disclosure.

In one embodiment, as shown in FIG. 34, spinal implant system 10, similar to the systems and methods described herein, includes an interbody implant 812, similar to the interbody implants described herein. Interbody implant 812 is unilaterally expandable, as described herein. Interbody implant 812 includes a member 814 and a member 816, similar to the members described herein. Member 816 is fixed in parallel with an actuator 846 that defines an axis X17, as described herein.

Member 814 and member 816 are connected by a linkage 834, similar to the linkages described herein. Member 814 includes a surface 830 that defines a cavity 832 configured for disposal of a portion of linkage 834, as described herein. Surface 830 defines a slot 836 and a slot 838 disposed contra-lateral to slot 836, similar to the slots described herein.

Slots 836, 838 are configured for disposal of a pin 840, similar to the pins described herein. As pin 840 translates within and relative to slots 836, 838, member 814 expands from member 816 in a first or initial zone of expansion of interbody implant 812, similar to that described herein. The first expansion zone includes an initial, first or selected amount of expansion, separation and/or spacing apart of member 814 relative to member 816 such that interbody implant 812 has an initial, first or selected height. Slots 836, 838 each include a ramp configuration to facilitate expansion of member 814 relative to member 816 in the first expansion zone. As pin 840 engages end points of slots 836, 838, pin 840 rotates relative to slots 836, 838 such that member 814 can expand from member 816 in a second zone of expansion via linkage 834, similar to that described herein. The second expansion zone includes a second or selected amount of expansion, separation and/or spacing apart of member 814 relative to member 816 in addition to or separate from the first expansion zone such that interbody implant 812 has a final, second or selected height.

Member 816 includes a housing 844. In some embodiments, housing 844 may be monolithically formed with member 816. In some embodiments, housing 844 may be integrally connected or include fastening elements for connection with member 816. In some embodiments, housing 844 is connected with member 814 via a pin 860. In some embodiments, pin 860 is configured as a pin hinge. Pin 860 is configured to facilitate pivoting of member 814 relative to member 816 for unilateral expansion of interbody implant 812. Housing 844 is configured for moveable disposal of actuator 846, similar to the actuators described herein. Housing 844 is configured for rotatable disposal of actuator 846 to facilitate expansion of member 814 relative to member 816, as described herein.

Linkage 834, similar to linkage 34, includes one or a plurality of links. Linkage 834 has a link, which includes an arm 850 and an arm 852. Arm 852 is spaced apart in relation to arm 850. Arms 850, 852 are configured for engagement with a pin 862 configured to facilitate pivoting of member 814 relative to member 816. Pin 862 is configured to connect arms 850, 852 with actuator 846 at a pivot axis PA5. Pivot axis PA5 is disposed transverse to axis X17 of actuator 846, as described herein. Pin 862 is connected with actuator 846 to actuate expansion of member 814 relative to member 816, as described herein.

Actuator 846 is engaged with a surgical instrument, such as, for example, a driver (not shown). The driver engages and rotates a screw 921. Screw 921 is threaded with, and rotates relative to and within housing 844 such that screw 921 translates relative to housing 844 to translate and/or drive pin 862 and pivot axis PA5 axially, similar to that described herein. Axial translation of pivot axis PA5 relatively, rotates arms 850, 852 to facilitate expansion and contraction of member 814 relative to member 816 about pivot axis PA5.

It will be understood that various modifications may be made to the embodiments disclosed herein. Therefore, the above description should not be construed as limiting, but merely as exemplification of the various embodiments, Those skilled in the art will envision other modifications within the scope and spirit of the claims appended hereto.

What is claimed is:

1. A spinal implant comprising:
   a housing defining a bore;
   a first member connected to the housing and comprising a first vertebral engaging surface and first and second slots;
   a first pin extending through the slots;
   a second member connected to the housing and comprising a second vertebral engaging surface opposite the first vertebral engaging surface;
   an actuator extending along a longitudinal axis between opposite first and second ends, the first end being positioned in the bore;
   a cap coupled to the second end;
   a linkage coupled to the first member, the linkage comprising spaced apart first and second arms; and
   a second pin extending through the cap and the arms,
   wherein the first pin is configured to translate within the slots to increase a distance between the first vertebral engaging surface and the second vertebral engaging surface and the actuator is rotatable relative to the housing to translate the second pin along the longitudinal axis to further increase the distance between the first vertebral engaging surface and the second vertebral engaging surface.

2. The spinal implant recited in claim 1, wherein:
   the first pin is configured to translate within the slots to expand the first member from the second member in a first zone of expansion; and
   wherein the actuator is rotatable relative to the housing to translate the second pin along the longitudinal axis to expand the first member from the second member in a second zone of expansion.

3. The spinal implant recited in claim 2, wherein:
   the first zone of expansion includes a first amount of spacing apart of the first vertebral engaging surface relative to the second vertebral engaging surface such that the implant has a first height; and
   the second zone of expansion includes a second amount of spacing apart of the first vertebral engaging surface relative to the second vertebral engaging surface in addition to the first zone of expansion such that the implant has a second height that is greater than the first height.

4. The spinal implant recited in claim 2, wherein:
   the first zone of expansion includes a first amount of spacing apart of the first vertebral engaging surface relative to the second vertebral engaging surface such that the implant has a first height; and
   the second zone of expansion includes a second amount of spacing apart of the first vertebral engaging surface relative to the second vertebral engaging surface separate from the first zone of expansion such that the implant has a second height that is greater than the first height.

5. The spinal implant recited in claim 2, wherein:
   the slots each include a ramp configuration; and
   the first pin engages end points of the slots such that the first pin rotates relative to the slots as the first member can expand from the second member in the second zone of expansion.

6. The spinal implant recited in claim 1, wherein the second member is monolithically formed with the housing.

7. The spinal implant recited in claim 1, wherein the second vertebral engaging surface extends parallel to the longitudinal axis before and after expansion of the implant.

8. The spinal implant recited in claim 1, wherein the linkage is disposed in a cavity of the first member defined by an inner surface of the first member that is opposite the first vertebral engaging surface.

9. The spinal implant recited in claim 1, wherein the actuator is a screw.

10. A spinal implant comprising:
    a housing defining a bore;
    a first member connected to the housing and comprising a first vertebral engaging surface and first and second slots, the second slot being coaxial with the first slot;
    a first pin extending through the slots;
    a second member connected to the housing and comprising a second vertebral engaging surface opposite the first vertebral engaging surface;
    an actuator extending along a longitudinal axis between opposite first and second ends, the first end being positioned in the bore;
    a cap coupled to the second end;
    a linkage coupled to the first member, the linkage comprising spaced apart first and second arms, the cap being positioned between the arms; and
    a second pin extending through the cap and the arms,
    wherein the first pin is configured to translate within the slots to increase an angle between the first vertebral engaging surface and the second vertebral engaging surface to a first angle and the actuator is rotatable relative to the housing to translate the second pin along the longitudinal axis to further increase the angle between the first vertebral engaging surface and the second vertebral engaging surface to a second angle.

11. The spinal implant recited in claim 10, wherein:
    the first pin is configured to translate within the slots to expand the first member from the second member in a first zone of expansion; and
    wherein the actuator is rotatable relative to the housing to translate the second pin along the longitudinal axis to expand the first member from the second member in a second zone of expansion.

12. The spinal implant recited in claim 11, wherein:
    the first zone of expansion includes a first amount of spacing apart of the first vertebral engaging surface relative to the second vertebral engaging surface such that the implant has a first height; and
    the second zone of expansion includes a second amount of spacing apart of the first vertebral engaging surface relative to the second vertebral engaging surface in addition to the first zone of expansion such that the implant has a second height that is greater than the first height.

13. The spinal implant recited in claim 11, wherein:
the first zone of expansion includes a first amount of spacing apart of the first vertebral engaging surface relative to the second vertebral engaging surface such that the implant has a first height; and
the second zone of expansion includes a second amount of spacing apart of the first vertebral engaging surface relative to the second vertebral engaging surface separate from the first zone of expansion such that the implant has a second height that is greater than the first height.

14. The spinal implant recited in claim 11, wherein:
the slots each include a ramp configuration; and
the first pin engages end points of the slots such that the first pin rotates relative to the slots as the first member can expand from the second member in the second zone of expansion.

15. The spinal implant recited in claim 10, wherein the second member is monolithically formed with the housing.

16. The spinal implant recited in claim 10, wherein the second vertebral engaging surface extends parallel to the longitudinal axis before and after expansion of the implant.

17. The spinal implant recited in claim 10, wherein the linkage is disposed in a cavity of the first member defined by an inner surface of the first member that is opposite the first vertebral engaging surface.

18. The spinal implant recited in claim 10, wherein the actuator is a screw.

19. The spinal implant recited in claim 10, wherein the slots each have an oblong configuration.

20. A spinal implant comprising:
a housing defining a bore;
a first member connected to the housing and comprising a first vertebral engaging surface and first and second slots, the second slot being coaxial with the first slot;
a first pin extending through the slots;
a second member connected to the housing and comprising a second vertebral engaging surface opposite the first vertebral engaging surface;
an actuator extending along a longitudinal axis between opposite first and second ends, the first end being positioned in the bore;
a cap coupled to the second end;
a linkage coupled to the first member, the linkage comprising spaced apart first and second arms, the cap being positioned between the arms; and
a second pin extending through the cap and the arms,
wherein the first member has a maximum length along the longitudinal axis equal to a maximum length of the second member along the longitudinal axis,
wherein the first pin is configured to translate within the slots to expand the first member from the second member in a first zone of expansion,
wherein the actuator is rotatable relative to the housing to translate the second pin along the longitudinal axis to expand the first member from the second member in a second zone of expansion, and
wherein the actuator is configured to translate the second pin along the longitudinal axis a distance along the longitudinal axis greater than maximum lengths of the slots along the longitudinal axis.

* * * * *